US012150783B2

(12) United States Patent
Vos et al.

(10) Patent No.: US 12,150,783 B2
(45) Date of Patent: Nov. 26, 2024

(54) HEARING DEVICE INCLUDING AN OPTICAL SENSOR

(71) Applicant: Sonion Nederland B.V., Hoofddorp (NL)

(72) Inventors: Eeuwe Jan Vos, Hoofddorp (NL); Dion Ivo De Roo, Hoofddorp (NL); Alwin Fransen, Hoofddorp (NL)

(73) Assignee: Sonion Nederland B.V., Hoofdorp (NL)

( * ) Notice: Subject to any disclaimer, the term of this patent is extended or adjusted under 35 U.S.C. 154(b) by 968 days.

(21) Appl. No.: 17/064,104

(22) Filed: Oct. 6, 2020

(65) Prior Publication Data

US 2021/0100508 A1   Apr. 8, 2021

(30) Foreign Application Priority Data

Oct. 7, 2019 (EP) .................................... 19201800
Jan. 31, 2020 (EP) .................................... 20154889

(51) Int. Cl.
*H04R 25/00* (2006.01)
*A61B 5/00* (2006.01)
*A61B 5/024* (2006.01)

(52) U.S. Cl.
CPC ........ *A61B 5/6817* (2013.01); *A61B 5/02427* (2013.01); *H04R 25/554* (2013.01); *H04R 25/70* (2013.01)

(58) Field of Classification Search
CPC ............ H04R 2225/025; H04R 25/554; H04R 25/603; H04R 25/65; H04R 25/70;
(Continued)

(56) References Cited

U.S. PATENT DOCUMENTS 5,517,574 A    5/1996 Tichy
6,788,796 B1   9/2004 Miles
(Continued)

FOREIGN PATENT DOCUMENTS

CN    104320748 A    1/2015
EP    2077091 A2    7/2009
(Continued)

OTHER PUBLICATIONS

European Patent Office, Extended European Search Report in European Application No. EP 20154889.8, dated Jul. 2, 2020 (10 pages).
(Continued)

*Primary Examiner* — Phylesha Dabney
(74) *Attorney, Agent, or Firm* — Nixon Peabody LLP

(57) ABSTRACT

A hearing device such as a receiver-in-ear assembly. The assembly includes a housing having a cavity extending through the housing; an optical transducer mounted in the cavity within a thickness of the housing, the optical transducer being mounted on a circuit board layer such that a spacing exists between a side of the optical transducer and a sidewall of the cavity. The circuit board layer extends underneath the housing and touching the housing such that the optical transducer is held within the cavity without touching the housing. The assembly further includes a protective substance forming a shield over the optical transducer and the cavity, the protective substance configured to affect a field of view of the optical transducer.

21 Claims, 22 Drawing Sheets

(58) Field of Classification Search
CPC .... H04R 1/1016; H04R 1/1091; H04R 2225/57; H04R 25/60; H04R 2225/023; A61B 5/6817; A61B 5/02427; A61B 5/0261; A61B 5/0816; A61B 5/14552; A61B 2562/0219; A61B 5/02055; A61B 5/02125; A61B 5/02416; A61B 5/02438; A61B 5/0533; A61B 5/14542; A61B 5/332
USPC ........................................................ 381/328
See application file for complete search history.

(56) References Cited

U.S. PATENT DOCUMENTS

| | | | |
|---|---|---|---|
| 6,831,577 B1 | 12/2004 | Furst |
| 6,853,290 B2 | 2/2005 | Jorgensen |
| 6,859,542 B2 | 2/2005 | Johannsen |
| 6,888,408 B2 | 5/2005 | Furst |
| 6,914,992 B1 | 7/2005 | van Halteren |
| 6,919,519 B2 | 7/2005 | Ravnkilde |
| 6,930,259 B1 | 8/2005 | Jorgensen |
| 6,943,308 B2 | 9/2005 | Ravnkilde |
| 6,974,921 B2 | 12/2005 | Jorgensen |
| 7,008,271 B2 | 3/2006 | Jorgensen |
| 7,012,200 B2 | 3/2006 | Moller |
| 7,062,058 B2 | 6/2006 | Steeman |
| 7,062,063 B2 | 6/2006 | Hansen |
| 7,072,482 B2 | 7/2006 | Van Doorn |
| 7,088,839 B2 | 8/2006 | Geschiere |
| 7,110,560 B2 | 9/2006 | Stenberg |
| 7,136,496 B2 | 11/2006 | van Halteren |
| 7,142,682 B2 | 11/2006 | Mullenborn |
| 7,181,035 B2 | 2/2007 | van Halteren |
| 7,190,803 B2 | 3/2007 | van Halteren |
| 7,206,428 B2 | 4/2007 | Geschiere |
| 7,221,767 B2 | 5/2007 | Mullenborn |
| 7,221,769 B1 | 5/2007 | Jorgensen |
| 7,227,968 B2 | 6/2007 | van Halteren |
| 7,239,714 B2 | 7/2007 | de Blok |
| 7,245,734 B2 | 7/2007 | Niederdraenk |
| 7,254,248 B2 | 8/2007 | Johannsen |
| 7,286,680 B2 | 10/2007 | Steeman |
| 7,292,700 B1 | 11/2007 | Engbert |
| 7,292,876 B2 | 11/2007 | Bosh |
| 7,336,794 B2 | 2/2008 | Furst |
| 7,376,240 B2 | 5/2008 | Hansen |
| 7,403,630 B2 | 7/2008 | Jorgensen |
| 7,415,121 B2 | 8/2008 | Mögelin |
| 7,425,196 B2 | 9/2008 | Jorgensen |
| 7,460,681 B2 | 12/2008 | Geschiere |
| 7,466,835 B2 | 12/2008 | Stenberg |
| 7,492,919 B2 | 2/2009 | Engbert |
| 7,548,626 B2 | 6/2009 | Stenberg |
| 7,657,048 B2 | 2/2010 | van Halteren |
| 7,684,575 B2 | 3/2010 | van Halteren |
| 7,706,561 B2 | 4/2010 | Wilmink |
| 7,715,583 B2 | 5/2010 | Van Halteren |
| 7,728,237 B2 | 6/2010 | Pedersen |
| 7,809,151 B2 | 10/2010 | Van Halteren |
| 7,822,218 B2 | 10/2010 | Van Halteren |
| 7,899,203 B2 | 3/2011 | Van Halteren |
| 7,912,240 B2 | 3/2011 | Madaffari |
| 7,946,890 B1 | 5/2011 | Bondo |
| 7,953,241 B2 | 5/2011 | Jorgensen |
| 7,961,899 B2 | 6/2011 | Van Halteren |
| 7,970,161 B2 | 6/2011 | van Halteren |
| 8,098,854 B2 | 1/2012 | van Halteren |
| 8,101,876 B2 | 1/2012 | Andreasen |
| 8,103,039 B2 | 1/2012 | van Halteren |
| 8,160,290 B2 | 4/2012 | Jorgensen |
| 8,170,249 B2 | 5/2012 | Halteren |
| 8,189,804 B2 | 5/2012 | Hruza |
| 8,189,820 B2 | 5/2012 | Wang |
| 8,223,996 B2 | 7/2012 | Beekman |
| 8,233,652 B2 | 7/2012 | Jorgensen |
| 8,259,963 B2 | 9/2012 | Stenberg |
| 8,259,976 B2 | 9/2012 | van Halteren |
| 8,259,977 B2 | 9/2012 | Jorgensen |
| 8,280,082 B2 | 10/2012 | van Halteren |
| 8,284,966 B2 | 10/2012 | Wilk |
| 8,313,336 B2 | 11/2012 | Bondo |
| 8,315,422 B2 | 11/2012 | van Halteren |
| 8,331,595 B2 | 12/2012 | van Halteren |
| 8,369,552 B2 | 2/2013 | Engbert |
| 8,379,899 B2 | 2/2013 | van Halteren |
| 8,509,468 B2 | 8/2013 | van Halteren |
| 8,526,651 B2 | 9/2013 | Lafort |
| 8,526,652 B2 | 9/2013 | Ambrose |
| 2010/0145135 A1 | 6/2010 | Ball |
| 2011/0182453 A1 | 7/2011 | van Hal |
| 2011/0189880 A1 | 8/2011 | Bondo |
| 2011/0299708 A1 | 12/2011 | Bondo |
| 2011/0299712 A1 | 12/2011 | Bondo |
| 2011/0311069 A1 | 12/2011 | Ambrose |
| 2012/0014548 A1 | 1/2012 | van Halteren |
| 2012/0027245 A1 | 2/2012 | van Halteren |
| 2012/0140966 A1 | 6/2012 | Mocking |
| 2012/0155683 A1 | 6/2012 | van Halteren |
| 2012/0155694 A1 | 6/2012 | Reeuwijk |
| 2012/0255805 A1 | 10/2012 | van Halteren |
| 2013/0028451 A1 | 1/2013 | de Roo |
| 2013/0136284 A1 | 5/2013 | van Hal |
| 2013/0142370 A1 | 6/2013 | Engbert |
| 2013/0163799 A1 | 6/2013 | van Halteren |
| 2013/0195295 A1 | 8/2013 | van Halteren |
| 2015/0366475 A1 | 12/2015 | Just et al. |
| 2018/0020979 A1 | 1/2018 | Wagner |
| 2018/0042554 A1* | 2/2018 | Wagner ............... A61B 5/1455 |

FOREIGN PATENT DOCUMENTS

| | | | | |
|---|---|---|---|---|
| EP | 2077091 A3 | 7/2009 |
| EP | 3057138 A1 | 8/2016 |
| EP | 2667768 B1 | 8/2017 |
| EP | 3407628 A1 | 11/2018 |
| EP | 3427657 A1 | 1/2019 |
| EP | 3525490 A1 | 8/2019 |
| JP | 5185265 B2 | 4/2013 |
| JP | 2014166215 A | 9/2014 |
| WO | WO 2016/022295 A1 | 2/2016 |
| WO | WO-2020060911 A1 * | 3/2020 | ........... A61B 5/0205 |

OTHER PUBLICATIONS

K/S HIMPP LLC; Notice of Opposition to European Patent Application No. 20199018.1, dated Sep. 7, 2023 (29 pages).
European Patent Office; Communication of a Notice of Opposition against European Patent Application No. 20199018.1, dated Sep. 13, 2023 (27 pages).
European Patent Office; Communication of notices of opposition against European Patent Application No. 20199018.1 and request to file observations, dated Sep. 22, 2023 (1 page).
European Patent Office; Communication of no further notices of opposition pursuant to Rule 79(2) EPC against European Patent Application No. 20199018.1, dated Sep. 22, 2023 (2 pages).
European Patent Office; Extended European Search Report for European Patent Application No. 23219906.7, dated May 7, 2024 (12 pages).
Examination Report in Chinese Patent Application No. 202011072231.5, in Chinese, dated Jun. 19, 2024 (9 pages).

* cited by examiner

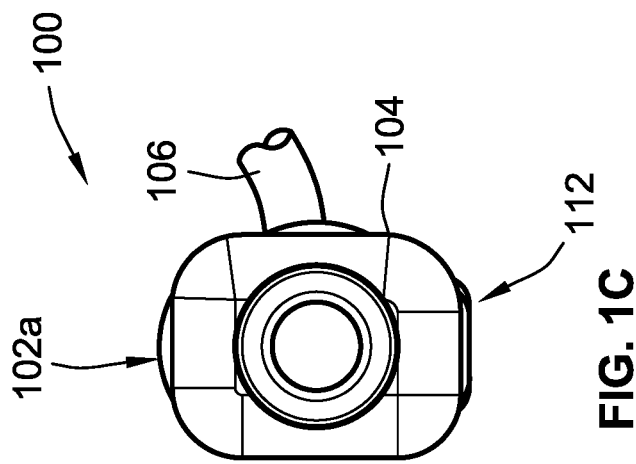
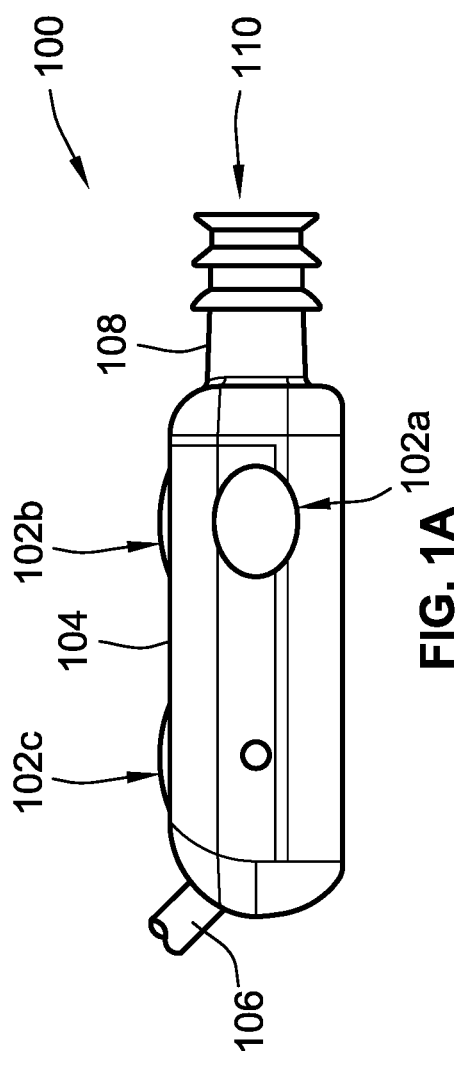
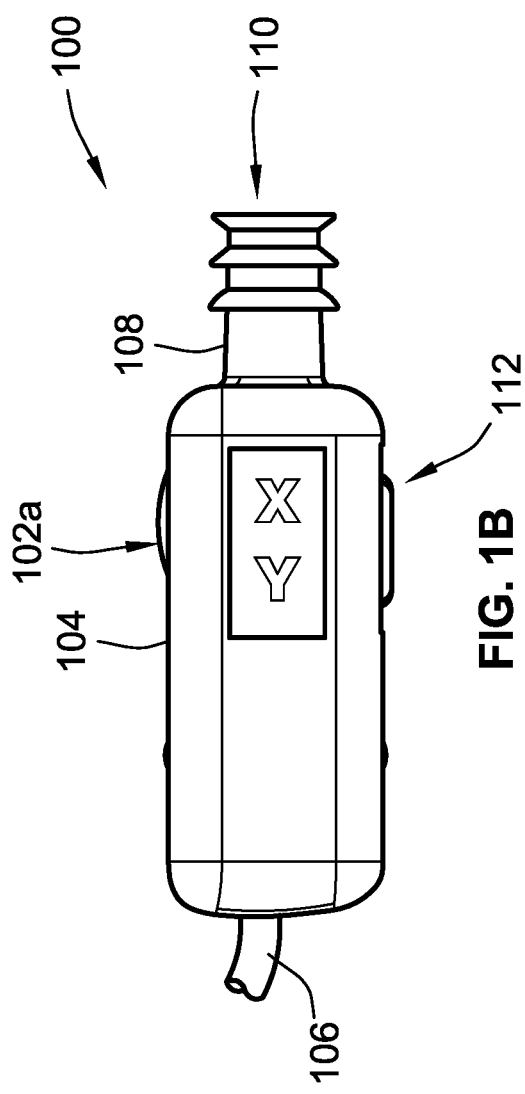

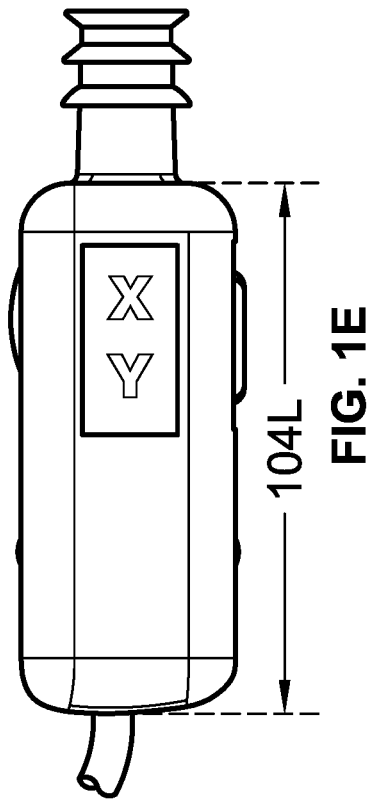
FIG. 1E
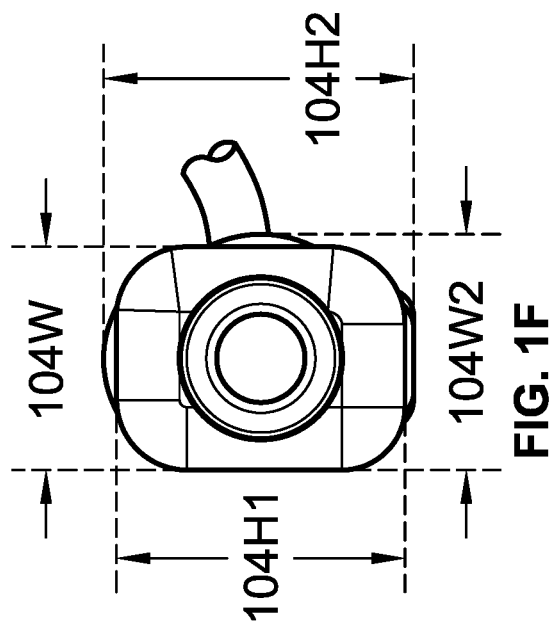
FIG. 1F
| Dimension | Range |
|---|---|
| 104L | 6-15mm |
| 104W | 2-8mm |
| 104W2 | 2-8mm |
| 104H1 | 2-8mm |
| 104H2 | 2-8mm |
| 103W | 2-5mm |
| 103H | 2-5mm |
FIG. 1G
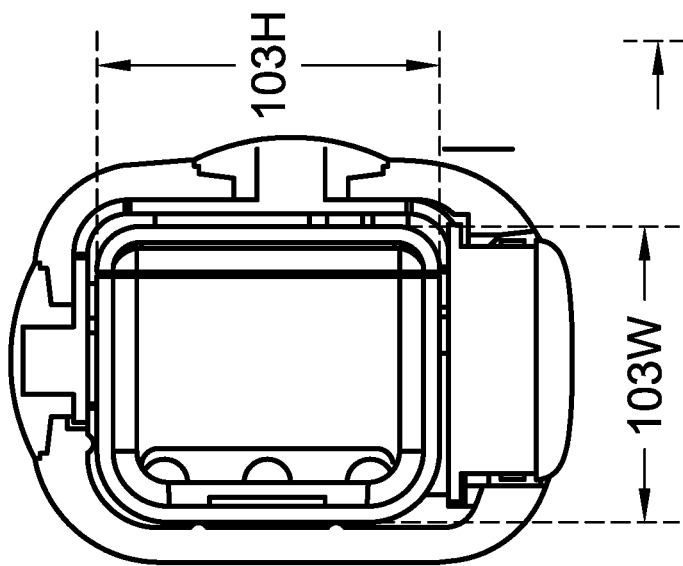
FIG. 1D

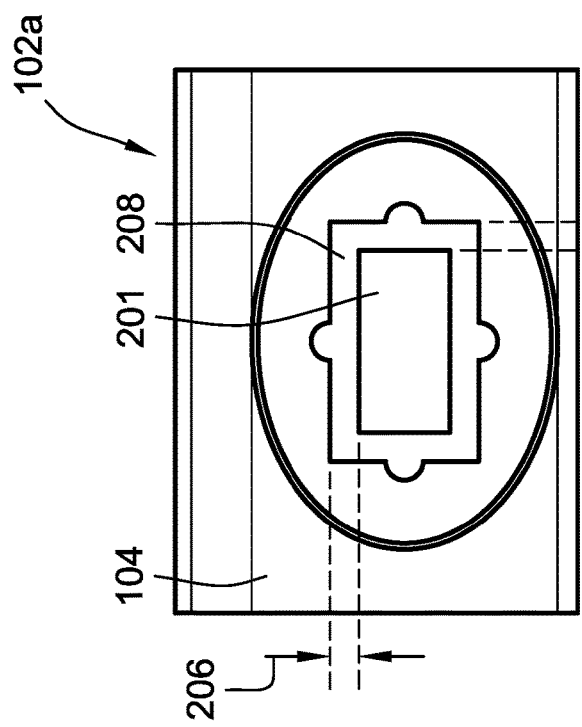
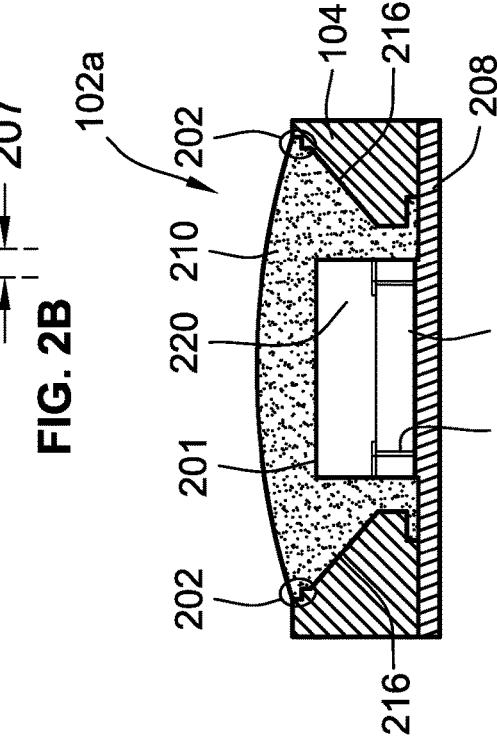
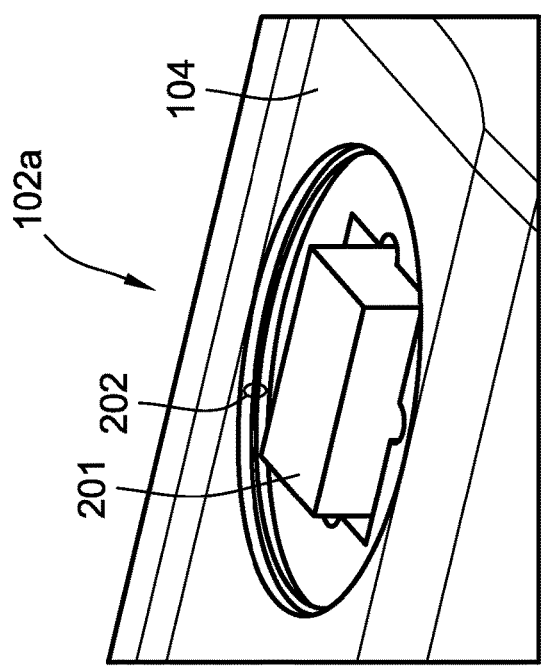
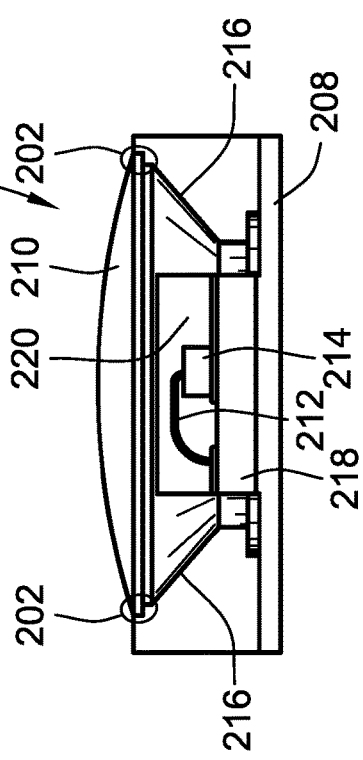
FIG. 2A
FIG. 2B
FIG. 2C
FIG. 2D

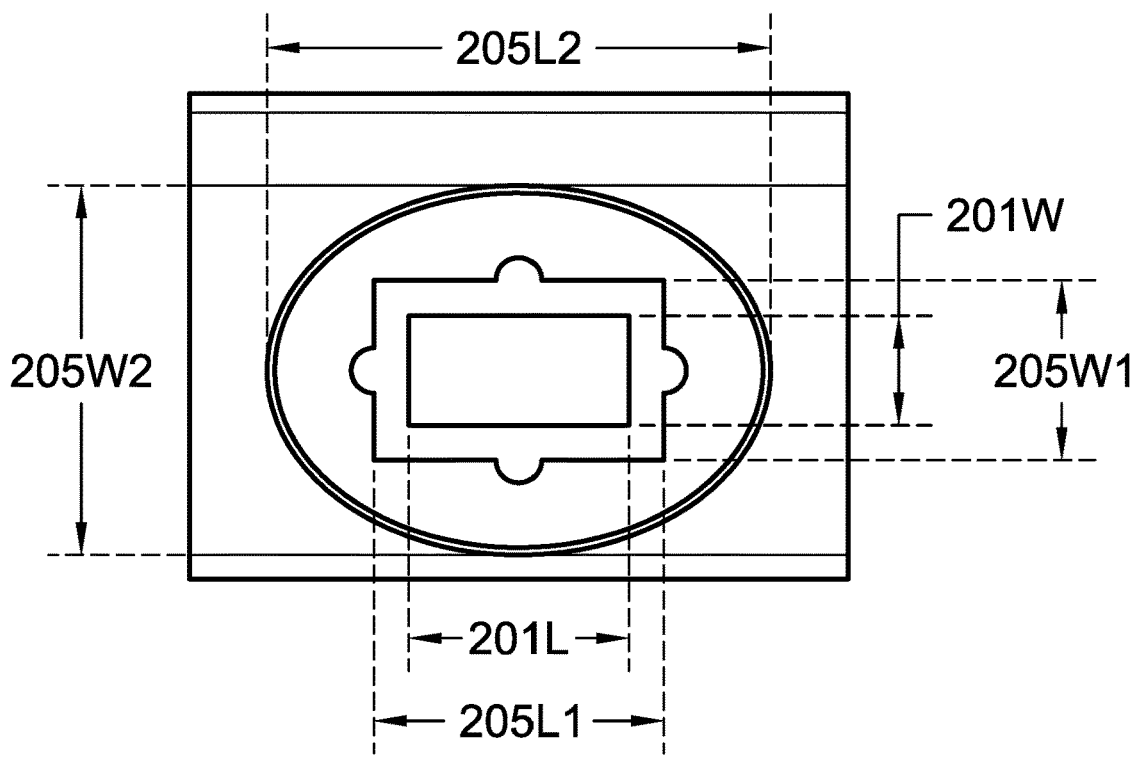
FIG. 2E
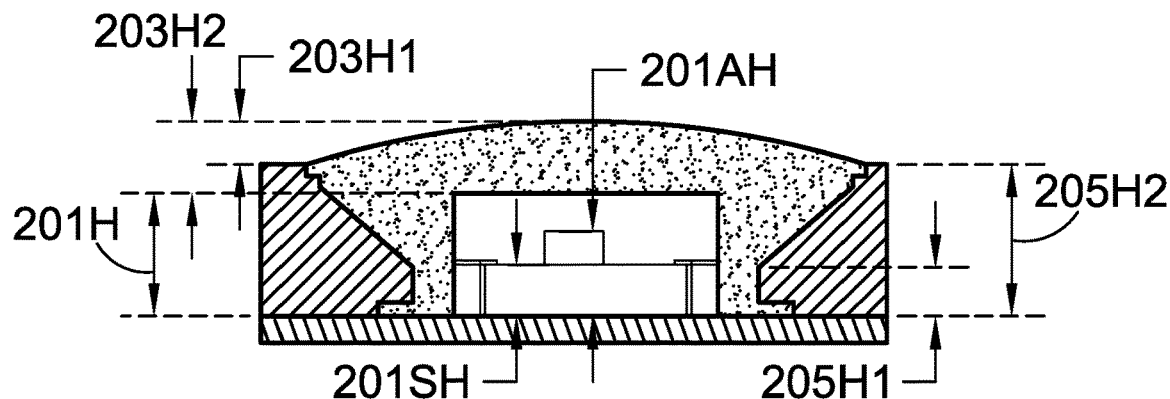
FIG. 2F
| Dimension | Range | Dimension | Range |
|---|---|---|---|
| 201L | 0.5-2mm | 205W1 | >0.25mm |
| 201W | 0.25-1mm | 205W2 | >0.25mm |
| 201H | 0.25-1mm | 203H1 | 0.05-0.3mm |
| 201SH | 0.1-0.3mm | 203H2 | 0-1.8mm |
| 201AH | 0.2-0.5mm | 205H2 | 0.1-0.5mm |
| 205L1 | 0.5-2mm | 205H1 | 0.05-0.1mm |
| 205L2 | 1-4mm | | |
FIG. 2G

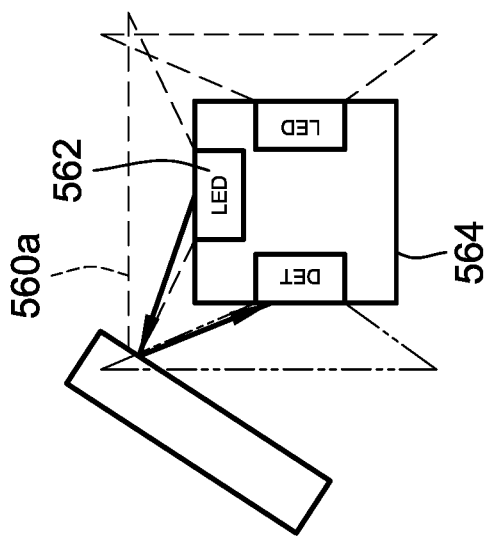
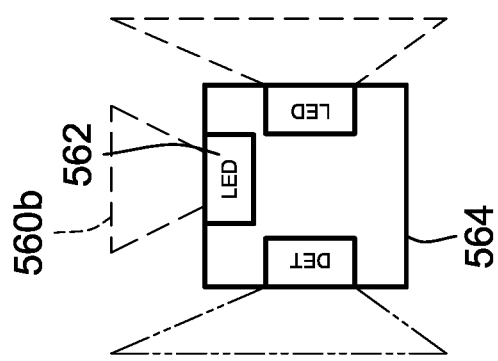
FIG. 5B
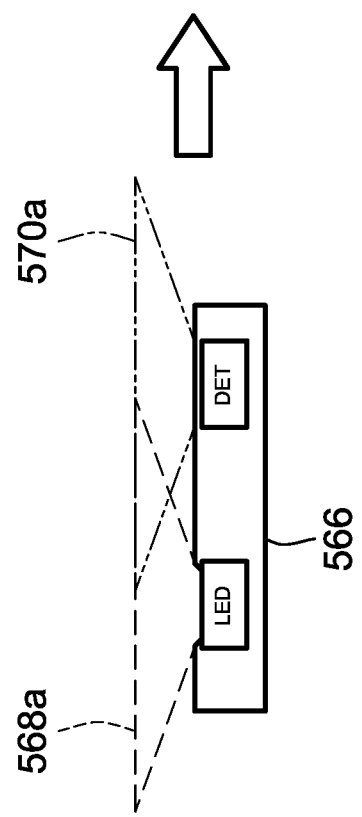
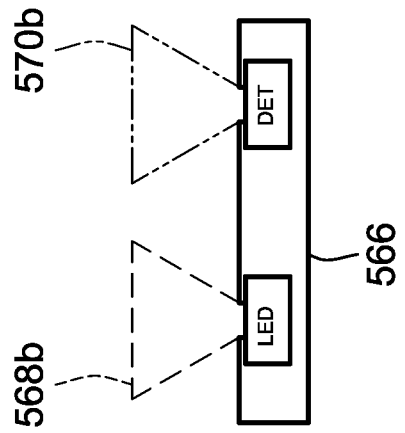
FIG. 5C

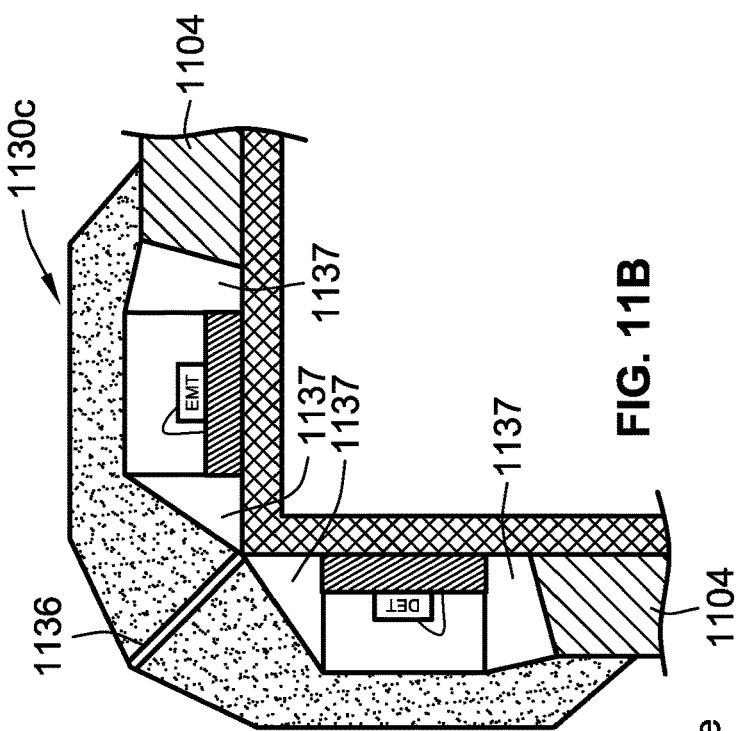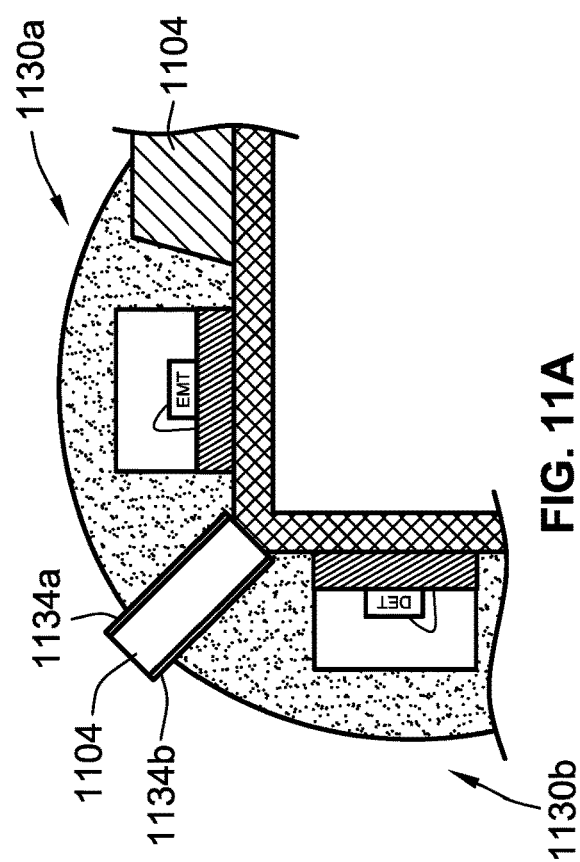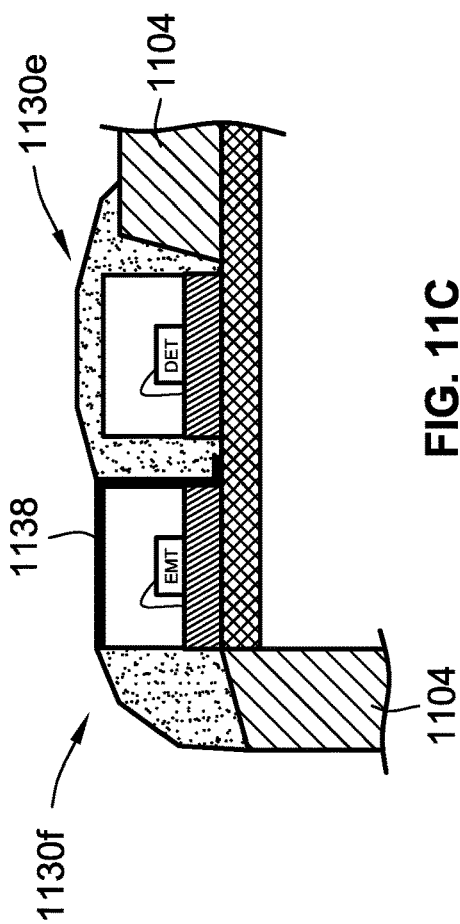
FIG. 11A
FIG. 11B
FIG. 11C

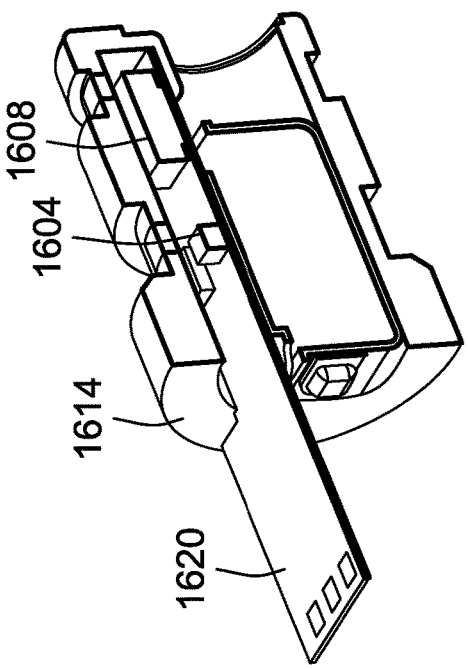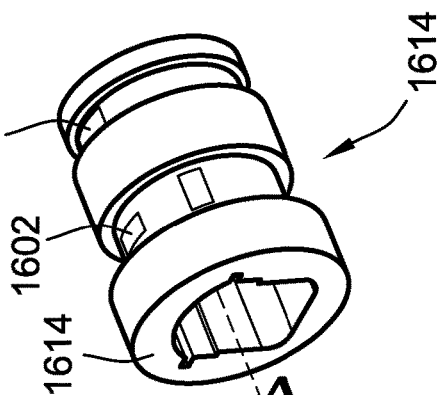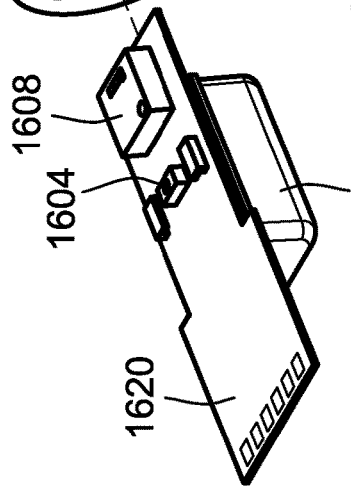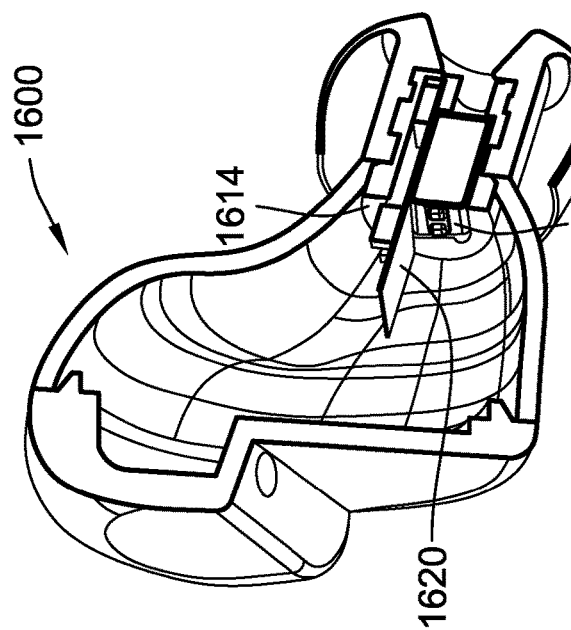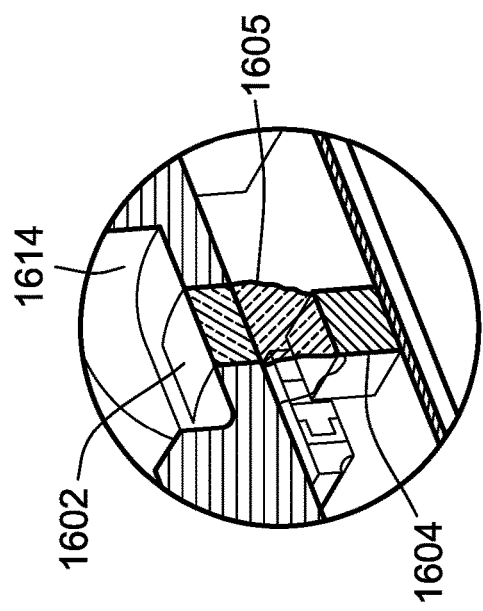

HEARING DEVICE INCLUDING AN OPTICAL SENSOR

CROSS-REFERENCE TO RELATED APPLICATIONS

This application claims the benefit of European Patent Application Serial No. 19201800.0, filed Oct. 7, 2019, and European Patent Application Serial No. 20154889.8, filed Jan. 31, 2020, both of which are incorporated herein by reference in their entireties.

FIELD OF THE INVENTION

The present disclosure relates to a hearing device such as a receiver-in-canal assembly or earbuds for positioning in or at an ear canal of a user. The receiver-in-canal assembly includes a housing with at least one cavity and at least one optical transducer mounted within the at least one cavity, such as within a thickness of the housing. The transducer may also lie just below (or above) the thickness of the housing. All embodiments will also be applicable to this position of the transducer.

BACKGROUND OF THE INVENTION

A receiver-in-canal hearing aid is a type of hearing aid that fits at least partially within an ear canal of a user. It includes a speaker or receiver that generates sounds within the ear canal of hearing impaired users. A receiver-in-canal assembly for positioning in or at an ear canal of a user usually does not include an optical sensor within its housing due to manufacturing challenges to miniaturize these sensors for the harsh environment within the ear. The present disclosure provides solutions for improving efficacy of optical sensors/systems embedded within receiver-in-canal assemblies and other hearing devices.

Receiver-in-ear assemblies usually do not include optical sensors for measuring physiological parameters of a user relating health or other conditions. Furthermore, even if an optical sensor is provided on a receiver-in-ear assembly, its efficacy is reduced because light beams from emitters within the optical sensor cannot be properly channeled or amplified to areas of interest within the ear of the user. This is because incorporating a light emitting diode (LED) or detector with an optical amplifier (e.g., a reflector) on a receiver-in-ear assembly is a challenging problem. Firstly, the LED or detector with an optical amplifier has a larger form factor compared to LEDs without optical amplifiers. Embodiments of the present disclosure provides solutions for at least solving this problem and other problems related to embedding optical sensors in receiver-in-ear assemblies.

SUMMARY OF THE INVENTION

A first aspect of the present disclosure provides a hearing device such as a receiver-in-ear assembly or earbud comprising:
  a housing comprising one or more wall portions defining an inner space and including a cavity extending through a wall portion of the housing;
  a receiver provided in the inner space,
  a circuit board layer,
  an optical transducer being mounted in the cavity, the optical transducer being mounted on the circuit board layer such that a spacing exists between a side of the optical transducer and a sidewall of the cavity; the circuit board layer extending underneath the wall portion and touching the wall portion such that the optical transducer is held within the cavity and
  a protective substance forming a shield over the optical transducer and the cavity, the protective substance configured to affect a field of view of the optical transducer.

The protective element or substance may be a protective substance configured to hermetically seal the assembly and/or affect a field of view of the emitter.

In another aspect, a hearing device is provided for positioning at or partially or fully in ear canal, the device comprising:
  a housing including a cavity extending through the housing;
  a transducer such as an optical emitter or detector or a sensor being at least partially mounted within a thickness of the housing at the cavity, the transducer being mounted such that a spacing exists between a side of the emitter and a sidewall of the cavity; and
  a protective element forming a shield over the transducer and the cavity.

The protective element or substance may be a protective substance configured to hermetically seal the assembly or cavity and/or affect the performance of the transducer.

In this context, a housing may be formed by one or more wall portions. The wall portions define an inner space which is at least partly delimited by the wall portions. An outer surface of the wall portions may form part of an outer surface of the housing and an inner surface of the wall portions may take part in the definition of the inner space.

A receiver is provided in the inner space. Thus, preferably a sound output is provided in the housing also extending from the inner space toward surroundings of the housing. A receiver is a sound generator, typically with dimensions so small that it may be used in hearing aids and RICs. Often, a receiver has a largest dimension of 8 mm or less. The receiver may comprise electrical conductors or the like for transmitting an electrical signal to the receiver. Such conductors may extend from the inner space and to surroundings of the housing.

The housing can have walls or wall portions of a predetermined thickness. Since the cavity extends through the housing wall portion, such as from the inner space to surroundings of the housing at least prior to providing of the transducer and protective element, incorporating an emitter in thin walled housings of receiver-in-ear assemblies is not an issue, as the emitter may be positioned in the cavity and thus not take up space in the inner space of the housing. If the wall portion is straight, the outer and inner surfaces thereof define parallel planes between which the transducer may be provided. In this context "within a thickness of the housing" means that the receiver is positioned inside the cavity and does not extend out of the cavity to any side thereof to extend outside of a thickness of the housing such as at the edges of the cavity.

The circuit board layer may be a so-called PCB and may be stiff or flexible. Often, the circuit board layer has conductors electrically connected to one or more conductors or connectors of the transducer. The circuit board layer extending underneath the wall portion and touching the wall portion such as being attached to or biased toward the wall portion. Then, the optical transducer is held within the cavity, such as fixed therein by engagement between the optical transducer and the circuit board and engagement between the circuit board and the wall portion. The circuit board may have a surface at which the optical transducer is provided and which engages the wall portion.

The transducer may be an emitter such as an LED for emitting photoplethysmogram (PPG) light of a selected wavelength or of multiple wavelengths. The emitter can be mounted in a manner such that a top of the emitter is in line with an outer surface of the housing. Alternatively, the transducer may be a light receiver. Actually, the transducer may comprise both an emitter and a detector/receiver.

Alternatively, multiple transducers may be provided each in a separate cavity, where one or more of the transducers is an emitter and one or more of the transducers is a receiver.

In an embodiment, the sidewall of the cavity includes one or more step portions, one or more straight portions, one or more slanted portions, or any combination thereof. The sidewall can have a straight portion which is substantially vertical for mounting the emitter in a tight fit fashion (with adjacent LED surfaces) and a slanted portion which is generally inclined to enable a desired angle of light emission of no more than 180 degrees depending on the field of view of the emitter. A cross-sectional profile of the sidewall can be piecewise linear with straight portions, slanted portions, etc.

In an embodiment, the sidewall is curved or parabolic shaped. Piecewise construction of the sidewall can also include not just straight portions as previously described but curved portions as well.

In an embodiment, the sidewall of the cavity includes one or more reflective surfaces. The reflective surfaces can reflect light, such as at least 30%, of the emitter at selected light wavelengths, such as red, green and/or near-infra red light and/or a wavelength of 850 nm.

In an embodiment, the one or more reflective surfaces include a suitable material such as plastic of a reflective color, a plastic with reflective particles, metal, a coated surface, or any combination thereof. Composition and surface structure of the one or more reflective surfaces and/or an angle of the one or more reflective surfaces can make the one or more reflective surfaces reflect light of different wavelengths at different reflective angles and different direct or diffuse beam shapes.

In an embodiment, the one or more reflective surfaces can extend below the housing. In some embodiments, all reflective surfaces are under the housing, allowing (at least) part of the housing to be made from a translucent or transparent material, e.g., a transparent plastic, glass, transparent ceramics, etc. The one or more reflective surfaces then may extend along an inner surface of the wall portion(s). In some embodiments, when using transparent material and reflective surfaces underneath the housing, reflective surfaces on the sidewalls or reflective surfaces on an outer surface of the sidewalls are not included in the receiver-in-ear assembly.

In some embodiments, the one or more reflective surfaces is provided under the emitter. In some embodiments, the one or more reflective surfaces is on an outer surface of the housing such as on an outer surface of one or more wall portions. Reflective surfaces according to embodiments of the disclosure can be made from separate reflective parts. Reflective surfaces according to embodiments of the disclosure can be made from a reflective coating or layer deposited or laminated on a surface of the housing, sidewalls, etc.

In an embodiment, the protective substance includes one or more sealing glues. At least one of the one or more sealing glues can fill the cavity and form the shield as an outwardly curved shield. A curvature of the outwardly curved shield can affect the field of view of the emitter. The one or more sealing glues can have different functions, e.g., sealing an inside of the cavity, protecting electronics and the emitter, providing an optical lens, etc. The one or more sealing glues can include potting material, overmould, epoxy/resin/poly urethane, etc.

Alternatively, or additionally, the protective substance can include a lens. The lens may be a plastic lens or a glass lens. The protective substance includes a Fresnel lens, the Fresnel lens forming the shield as a flat surface.

In an embodiment, the radiating element of the emitter is positioned a distance from the circuit board layer such that increasing the distance increases the field of view of the emitter.

Another aspect of the present disclosure provides a hearing device such as a receiver-in-ear assembly or earbud comprising:
　a housing including a cavity extending through the housing;
　an emitter or detector being at least partially mounted within a thickness of the housing at the cavity, the emitter being mounted on a circuit board layer such that a spacing exists between a side of the emitter and a sidewall of the cavity;
　the circuit board layer extending underneath the housing and touching the housing such that the emitter or detector is held within the cavity without touching the housing; and
　a protective element forming a shield over the emitter and the cavity.

Clearly, all above considerations, embodiments and situations are equally relevant in this context.

Another aspect of the present disclosure provides a receiver-in-ear assembly comprising:
　a housing including a cavity extending through the housing, the housing being made from a transparent material; the housing may comprise one or more wall portions defining an inner space in which a receiver may be provided;
　an emitter being mounted within a thickness of the housing at the cavity or in the cavity, the emitter being mounted on a circuit board layer such that a spacing exists between a side of the emitter and a sidewall of the cavity;
　the circuit board layer extending underneath the housing or the housing wall portion at the inner space and including a reflective surface, the reflective surface touching the housing or wall portion such that the emitter is held within the cavity without touching the housing; and
　a protective substance forming a shield over the emitter and the cavity.

Again, all above considerations, embodiments and situations are equally relevant in this context.

The protective substance may be configured to affect a field of view of the emitter.

A final aspect of the present disclosure provides an assembly for a device to be worn at or in an ear canal, comprising:
　a housing (904), which may comprise one or more wall portions defining an inner space, including a cavity extending through the housing (904), such as through a wall portion of the housing (904), the housing (904) or the wall portion at least partly being made from a transparent material;
　an optical transducer (901) being mounted in or at the cavity, the optical transducer (901) being mounted on a circuit board layer (908) such that a spacing exists between a side of the optical transducer (901) and a sidewall (916) of the cavity;

a reflective surface (953) extending underneath the housing (904) or the wall portion, such as at a side at the inner space, the reflective surface (953) touching the housing (904) or wall portion; and a protective substance (910) forming a shield over the optical transducer (901) and the cavity, the protective substance (910) may be configured to affect a field of view of the optical transducer (901).

The foregoing and additional aspects and implementations of the present disclosure will be apparent to those of ordinary skill in the art in view of the detailed description of various embodiments and/or implementations, which is made with reference to the drawings, a brief description of which is provided next.

The foregoing and other advantages of the present disclosure will become apparent upon reading the following detailed description and upon reference to the drawings.

BRIEF DESCRIPTION OF THE DRAWINGS

FIGS. 1A, 1B, and 1C illustrate a receiver-in-canal assembly from different perspectives according to an embodiment of the present disclosure;

FIGS. 1D, 1E, and 1F illustrate the receiver-in-canal assembly of FIG. 1A with dimensional labels;

FIG. 1G is a table providing example ranges for the dimensional labels of FIGS. 1D, 1E, and 1F;

FIG. 2A illustrates a perspective view of an emitter positioned within a cavity in a housing of the receiver-in-canal assembly of FIG. 1A without a protective substance;

FIG. 2B illustrates a top view of the emitter in FIG. 2A;

FIG. 2C illustrates a side cutout view of the emitter in FIG. 2A;

FIG. 2D illustrates a cross-sectional view of the emitter in FIG. 2A;

FIGS. 2E and 2F illustrate views of the emitter in FIG. 2B and FIG. 2D, respectively, with dimensional labels;

FIG. 2G is a table providing example ranges for the dimensional labels of FIGS. 2E and 2F;

FIGS. 5B and 5C illustrate concept of narrowing field of view according to an embodiment of the present disclosure;

FIGS. 11A, 11B, and 11C illustrate examples of using reflectors to reduce separation between emitters and detectors according to some embodiments of the present disclosure;

FIG. 16A illustrates a cross-sectional view of an earbud with optical sensors according to some embodiments of the present disclosure;

FIG. 16B illustrates a cross-sectional view of electronic components of the earbud in FIG. 16A;

FIG. 16C illustrates an embodiment of a separation between an emitter and a window in the earbud of FIG. 16A;

FIG. 16D illustrates a nozzle and electronic components of the nozzle used in the earbud of FIG. 16A;

DETAILED DESCRIPTION OF THE INVENTION

Figure 3:
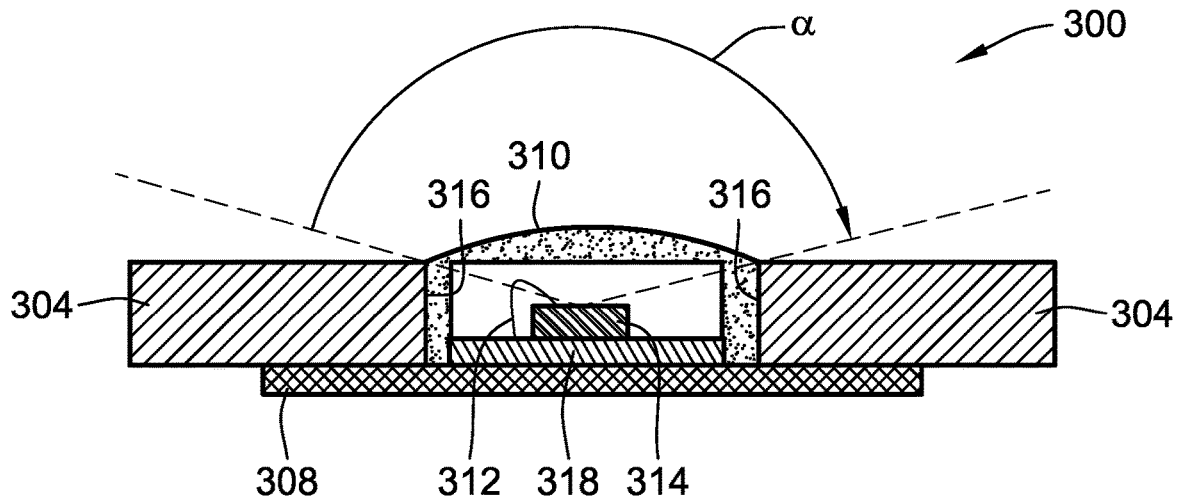
FIG. 3 illustrates an emitter location within a cavity of a housing of a receiver-in-canal assembly according to an embodiment of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

Hearing aids and similar devices are designed to improve hearing by making sound audible to a person with hearing loss. In some instances, a person with hearing loss continually gets worse over the course of using hearing aid devices and systems if the hearing aid devices and systems are not properly calibrated. As such, there should be methods and systems that can monitor at least a portion of the person's auditory system while using a hearing aid device. Receiver-in-canal hearing aid devices are hearing aid devices designed to place a receiver (speaker) inside the ear canal of a patient. The receiver is configured to produce amplified sounds captured from the environment outside of ear by a microphone or some wireless device.

Introducing electronics into an ear canal of a patient can be challenging to both designers of the electronics and the patient. The patient may be concerned with comfort, efficacy of the electronics, stylishness and aesthetics of the electronics, discreetness of the electronics, intrusion of the electronics into regular routine, etc. The designers may be concerned with energy requirements of the electronics, protecting the electronics from moisture and earwax, overall efficacy of the electronics, etc.

Although there may be other overlaps between concerns of the patient and the designers, efficacy of the hearing aid devices is important to both. Efficacy of hearing aid devices can depend on electronic components being used and the biology of the patient. Electronic components can wear out over time, and a patient can become acclimated to stimuli over time thus requiring higher and higher intensities for similar results. There are other sources of changes to a patient's body. For example, a patient can develop complications due to problems with oxygen getting to the tissue, a patient's body might develop resistance to constantly being stimulated in a same area, and so on. There should be ways of monitoring changes in tissue surrounding the ear canal or monitoring vitals within the ear canal to determine how the patient's body is responding over time to hearing aid stimuli. Embodiments of the present disclosure provide a system and method for using an emitter-detector system integrated with a receiver-in-canal hearing aid assembly to monitor a patient. The emitter-detector system can provide biometric information, e.g., heartrate and blood pressure.

An example emitter-detector system for monitoring tissue includes photoplethysmogram (PPG) sensors. A PPG sensor can be a pulse oximeter which illuminates skin and measures changes in light absorption. For example, a light emitting diode (LED) can be used to illuminate skin and a photodetector or photodiode can be used to measure changes in light absorption after the light from the LED interacts with the skin. PPG sensors have numerous applications. PPG sensors monitor blood volume changes in microvascular bed of tissue. PPG sensors can be used for monitoring blood pressure, monitoring heartrate and cardiac cycle of a patient, monitoring respiration of a patient, etc. Embodiments of the present disclosure provide an emitter-detector system small enough to be incorporated in an in-ear or in-ear-canal worn device, including a receiver-in-canal hearing aid assembly for continuous monitoring of a patient, also may be incorporated in any device, RIC, ITE, ITC, earbud, also without receiver/miniature speaker. Although a receiver-in-canal hearing aid assembly is used as an example in describing embodiments of the present disclosure, some embodiments can be applied to in the canal (ITC) and in the ear (ITE) hearing instruments or in situations where no receiver is present.

FIGS. 1A, 1B, and 1C illustrate a receiver-in-canal assembly 100 from different perspectives according to an embodiment of the present disclosure. Referring to FIG. 1A, a top plan view of the receiver-in-canal assembly 100 is provided. The receiver-in-canal assembly 100 includes a housing 104 of a certain thickness. The housing 104 is a protective covering for electronics and receiver (not shown) provided within the receiver-in-canal assembly 100. The receiver-in-canal assembly 100 can include a cable 106 for connecting electronics within the receiver-in-canal assembly 100 to other electronic components outside of the receiver-in-canal assembly 100. The receiver-in-canal assembly 100 includes a spout member 108. The spout member 108 includes a hollow spout channel 110 for guiding sound from a receiver provided within the receiver-in-canal assembly 100 to the ear canal. The receiver-in-canal assembly 100 also includes one or more emitter locations 102a, 102b, 102c, . . . , for placing one or more emitters. The one or more emitter locations 102a, 102b, 102c, . . . , are cavities in the housing 104.

Referring to FIG. 1B, a side view of the receiver-in-canal assembly 100 is provided. The side view illustrates one detector location for placing a detector 112 on the receiver-in-canal assembly 100. Referring to FIG. 1C, a front view of the receiver-in-canal assembly 100 is provided. The front view is from the perspective of looking into the hollow spout channel 110. Although three emitter locations and one detector location is provided in FIGS. 1A-1C, it is understood that any number of emitter locations and any number of detector locations can be provided around the receiver-in-canal assembly 100. Three emitter locations and one detector location is merely provided as an example. Furthermore, emitters and detectors can be on a same side or surface of a receiver-in-canal assembly. Emitters and detectors can be located on opposite sides or surfaces of a receiver-in-canal assembly. Emitters and detectors can be located on adjacent sides or surfaces of a receiver-in-canal assembly. Emitters and detectors can be placed on a front (close to a tympanic membrane) or on a back of a receiver-in-canal assembly. Emitters and detectors can be oriented to have a field of view in any direction (up/down/front/back/left/right) with any angle compared to housing surfaces of a receiver-in-canal assembly.

FIGS. 1D, 1E, and 1F illustrate the receiver-in-canal assembly of FIG. 1A with dimensional labels. FIG. 1D illustrates a cross section from a back view of the receiver-in-canal assembly 100. FIG. 1D identifies a receiver height 103H and a receiver width 103W. FIG. 1E illustrates a housing portion length 104L of the receiver-in-canal assembly 100. FIG. 1F illustrates a housing portion width 104W, a housing portion height 104H1, and a housing portion height with bumps 104H2.

FIG. 1G is a table providing example ranges for the dimensional labels of FIGS. 1D, 1E, and 1F. The housing portion length 104L can range from 6 to 15 mm. The housing portion width 104W can range from 2 to 8 mm. The housing portion height 104H1 and the housing portion height with bumps 104H2 can range from 2 to 8 mm. An example value for the housing portion length 104L by the housing portion width 104W by the housing portion height 104H1 is 11.0 mm×3.5 mm×4.6 mm. The housing portion height with bumps 104H2 for the previous example can be 5.0 mm.

The receiver height 103W and the receiver width 103H can range from 2 to 5 mm. In some embodiments, dimensions for the receiver height 103W by the receiver width 103H include 2.7 mm×0.98 mm, 2.7 mm×1.96 mm, 3.1 mm×2.55 mm, 2.8 mm×4.09 mm, etc. Receivers can have a length that ranges from 5 mm to 8 mm.

FIG. 2A illustrates a perspective view of an emitter 201 positioned within a cavity in the housing 104 of the receiver-in-canal assembly 100. The perspective view does not show a protective covering for the cavity. The cavity can have a stepped design 202. Referring to FIG. 2B, a top view of the emitter 201 is provided. Other than the stepped design 202, the cavity can include spacing, e.g., a spacing 206 and a spacing 207, between the housing 104 and the emitter 201. The spacing 206 and the spacing 207 can be, e.g., 0.15 mm. The spacing 206 and the spacing 207 can serve as positioning tolerances for the emitter 201. Furthermore, the spacing 206 and 207 can serve as capillary distances/gaps for a protective filling, e.g., glue, that holds the emitter 201 in place. The cavity in the housing 104 exposes a circuit board layer 208. The circuit board layer 208 can be a flexible circuit board comprising a flexible polymer.

Referring to FIG. 2C, a side cutout view of the emitter 201 in FIG. 2A is provided. Examples of the emitter 201 include a transmitter for transmitting electromagnetic waves, an LED, an exit of an optical fiber/lightguide (transmitting light generated at a different location), etc. In an example where the emitter 201 is an LED, from the side cutout view of FIG. 2C, the emitter 201 can have within it an active or radiating element 214 and a wire 212 for connecting the radiating element 214 to a power source. The emitter 201 can have a ceramic base 218 for providing structure to the radiating element 214. A height of the ceramic base 218 can be used to adjust a height of the radiating element 214 in relation to a height or thickness of the housing 104. The emitter 201 can have a clear LED coating 220 to protect the radiating element 214 and the wire 212 from environmental and physical influences. The clear LED coating 220 can be a clear glue or overmould.

In FIG. 2C, the emitter 201 is covered with a protective substance 210. The protective substance 210 fills in spaces within the cavity in the housing 104. The protective substance 210 can be a glue that contours to the spaces within the cavity. In some embodiments, the protective substance 210 is a glue that forms a lens that directs beams of light coming from the emitter 201. The protective substance 210 is applied to cover all corners and surfaces of the emitter 201.

The cavity in FIG. 2C is shown to have sidewalls 216. The sidewalls 216 are slanted. The cavity also includes the stepped design 202. Although two steps are shown in the stepped design 202, more than two steps can be provided in the cavity. The stepped design 202 enables the protective substance 210 to remain within the cavity during manufacturing, fostering the protective substance 210 to form a dome around the cavity.

Referring to FIG. 2D, a cross-sectional view of the emitter 201 is provided without the radiating element 214 and the wire 212. As shown in FIG. 2D, the cavity completely penetrates the housing 104 such that within the cavity, the emitter 201 rests on the circuit board layer 208 and not on the housing 104. An inner surface of the housing 104 interfaces with the circuit board layer 208. Also shown in FIG. 2D, the ceramic base 218 of the emitter 201 is shown to have electrical channels 217 that connect to the circuit board layer 208.

FIG. 2E is a reproduction of FIG. 2B with dimensional labels, and FIG. 2F reproduces FIG. 2D with dimensional labels. FIG. 2G provides example ranges for the dimensional labels of FIGS. 2E and 2F. An emitter width 201W can range from 0.25 mm to 1 mm. An emitter length 201L and an emitter height 201H can range from 0.5 mm to 2 mm. A ceramic base height 201SH of an emitter can range from 0.1 mm to 0.3 mm. An active height 201AH including a ceramic base and a radiating element can range from 0.2 mm to 0.5 mm. A bump protruding height 203H1 of a protective substance can range from 0.05 mm to 0.3 mm, and a protruding substance height 203H2 from a top of an emitter can be between 0 mm and 1.8 mm.

FIGS. 2E and 2F show a cavity with sidewalls. A bottom width 205W1 and a top width 205W2 of the cavity can be above 0.25 mm. A bottom length 205L1 of the cavity can range from 0.5 mm to 2 mm, and a top length 205L2 of the cavity can range from 1 mm to 4 mm. A flat sidewall height 205H1 of a flat portion of the sidewall of the cavity can range from 0.05 mm to 0.1 mm. A slanted sidewall height 205H2 of a slanted portion of the sidewall of the cavity which also includes the flat sidewall height 205H1 can range from 0.1 mm to 0.5 mm.

For an example device, dimension for the emitter width 201W by the emitter length 201L by the emitter height 201H is 0.5 mm×1 mm×0.45 mm. Also dimensions for the ceramic base height 201SH is 0.18 mm and that for the active height 201AH is 0.33 mm. The bump protruding height 203H1 can be 0.33 mm, and the protruding substance height 203H2 can be 0.4 mm. The bottom width 205W1 and the top width 205W2 of the cavity can be 0.8 mm and 1.7 mm, respectively. The bottom length 205L1 and the top length 205L2 of the cavity can be 1.3 mm and 2.3 mm, respectively. The flat sidewall height 205H1 and the slanted sidewall height 205H2 can be 0.1 mm and 0.5 mm, respectively.

FIG. 3 illustrates an emitter location 300 within a cavity of a housing 304 of a receiver-in-canal assembly according to an embodiment of the present disclosure. The cavity is shown to have straight sidewalls 316. Within the cavity is an emitter with a radiating element 314 on a ceramic base 318. The radiating element 314 is connected to a circuit board layer 308 via a wire 312. A protective cover 310 is provided according to embodiments of the present disclosure. The radiating element 314 being positioned in the configuration of FIG. 3 is shown to have a field of view (FoV) governed by the angle $\alpha$. The angle $\alpha$ can be designed based on the thickness of the housing 304, the position of the radiating element 314 relative to the housing 304, and the shape formed by protective element 310. The higher the position of the radiating element 314 relative to the housing 304, the larger the angle $\alpha$, indicating a larger FoV.

Figure 4:
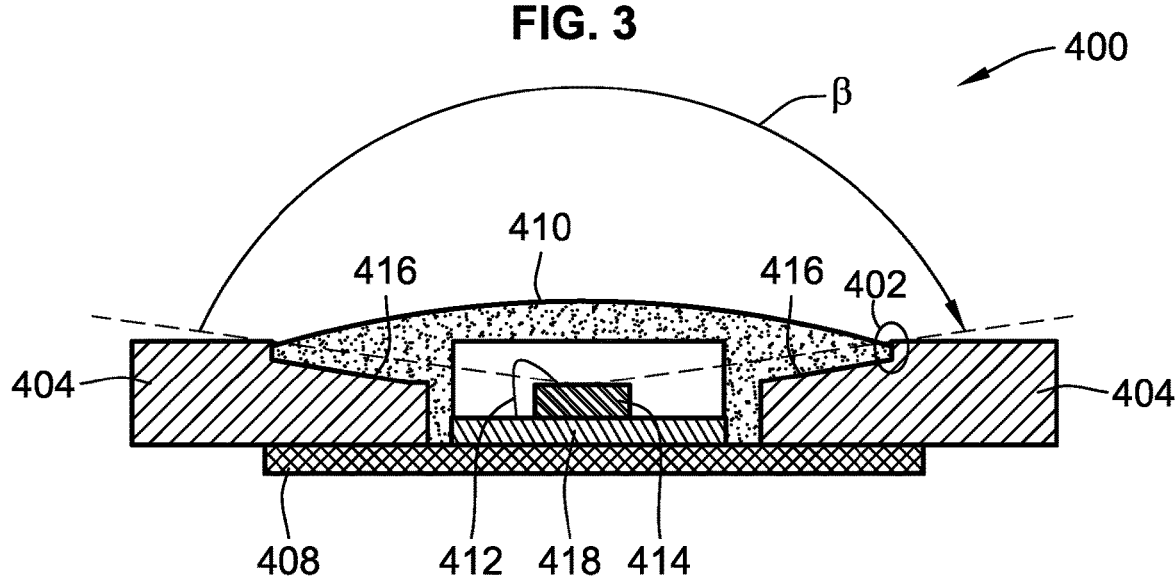
FIG. 4 illustrates an emitter location within a cavity of a housing of a receiver-in-canal assembly according to an embodiment of the present disclosure.

FIG. 4 illustrates an emitter location 400 within a cavity of a housing 404 of a receiver-in-canal assembly according to an embodiment of the present disclosure. The cavity is shown to have slanted sidewalls 416 with a step 402. Although one step is shown in FIG. 4, there can be one or more steps as shown above with respect to FIG. 2A. Within the cavity is an emitter with a radiating element 414 on a ceramic base 418. The radiating element 414 is connected to a circuit board layer 408 via a wire 412. A protective cover 410 is provided according to embodiments of the present disclosure. The radiating element 414 being positioned in the configuration of FIG. 4 is shown to have a field of view (FoV) governed by the angle $\beta$. The angle $\beta$ can be designed based on the thickness of the housing 404, the position of the radiating element 414 relative to the housing 404, the shape formed by protective element 410, the angle of the slant the slanted sidewalls 416, size of the step 402.

Comparing FIG. 4 to FIG. 3, addition of the slanted sidewalls 416 and the step 402 indicates that the angle $\beta$ can be designed to be larger than the angle α. As such, the radiating element 414 will have a larger FoV compared to the radiating element 314. Furthermore, a larger angle β compared to the angle α ensures that the design in FIG. 4 has a larger radius of protective substance when compared to FIG. 3. The larger radius indicates a lower curvature of the surface of the protective substance. An advantage is that less light from the radiating element 414 is reflected at the boundary of the protective substance 410 when compared to light from the radiating element 314 reflected at the boundary of the protective substance 310.

The angle α and the angle β can further be adjusted based on a relative positioning of the radiating elements 314 and 414, respectively, to outer edges of the respective cavities of FIG. 3 and FIG. 4. For example, in FIG. 3, the radiating element 314 lies below an outer surface of the housing 304 such that the sidewalls 316 restrict the FoV to the angle α. On the other hand, in FIG. 4, the radiating element 414 also lying below the surface of the housing 404 has the slanted sidewalls 416 and the step 402 such that the angle β is larger than alpha. If the radiating elements 314 and 414 were positioned relatively higher in comparison to the housing 304 and 404, respectively, then the angles α and β would increase. The positioning of the radiating elements 314 and 414 is limited by a maximum size of their respective receiver-in-canal assemblies. That is, a receiver-in-canal assembly should fit the smallest ear canals, thus there is a maximum width and a maximum height for the receiver-in-canal assembly. In some embodiments, emitters are designed to be sunken into cavities as shown in FIG. 3 and FIG. 4 so that a maximum size of a receiver-in-canal assembly is not violated.

Figure 5A:
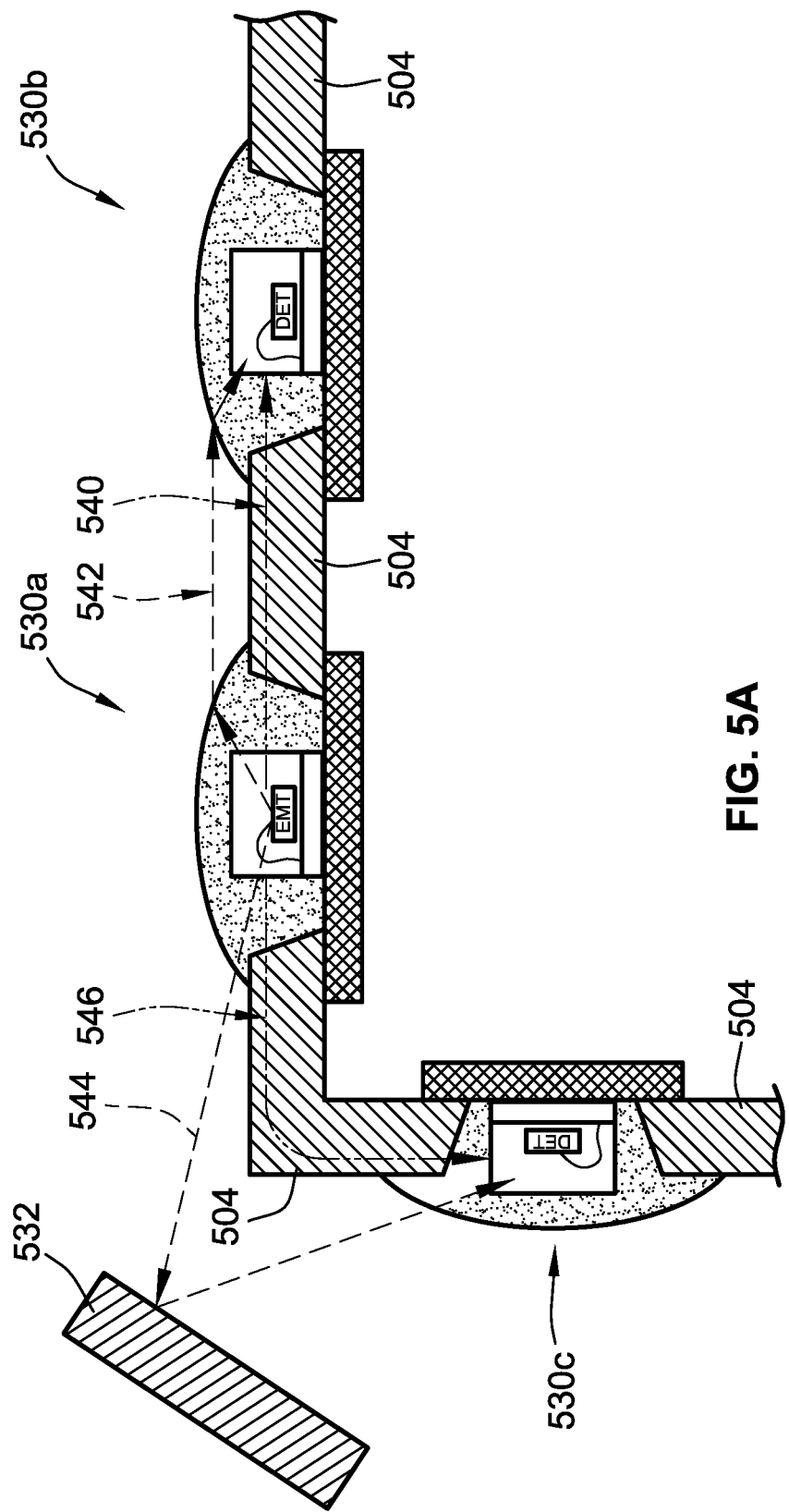
FIG. 5A illustrates an emitter-detector system embedded within a receiver-in-canal assembly and light paths from an emitter unit to detectors units according to an embodiment of the present disclosure.

Having a wide FoV can introduce some disadvantages. For example, FIG. 5A illustrates a cross-sectional view of a receiver-in-canal assembly with an emitter unit 530a and detector units 530b and 530c embedded within a housing 504 of the receiver-in-canal assembly. FIG. 5A also illustrates light paths from the emitter unit 530a to the detector units 530b and 530c. Examples of the emitter unit 530a include those already described with respect to any of FIGS. 2A-2D, 3 and 4. The detector units 530b and 530c can take similar form and shape to the emitter unit 530a, except that instead of a radiating element (EMT) being the active element, an absorbing element (DET) is the active element. An absorbing element can be a photodetector, an electromagnetic receiver, etc. The detector units 530b and 530c can also look different from the emitter unit 530a. For example, the detector units 530b and 530c can have a flat window, can include glue or not include glue, can include reflectors or not include reflectors, etc.

Desired operation of emitter-detector systems involves having an emitter emit signals that interact with a test object then having the detector detect the signals after the interaction with the test object. Signals that do not interact with the test object distort accuracy and introduce errors to the results obtained from emitter-detector systems. In FIG. 5A, the emitter unit 530a radiates signals according to a FoV. The desired signals that should reach the detector units 530b and 530c should interact with tissue within the ear, for example, an ear canal wall 532. That is, a light signal 544 from the emitter unit 530a that reaches the ear canal wall 532 and then interacts with the ear canal wall 532 before reaching the detector 530c is a desired signal. There are multiple ways that signals generated by the emitter unit 530a can distort measurement results. For example, a light signal 540 can pass through the housing 504 to reach the detector unit 530b. Similarly, a light signal 546 can be guided through the housing 504 to reach the detector unit 530c. In another example, a light signal 542 can travel directly from the emitter unit 530a to the detector unit 530b.

There are multiple ways to alleviate the problems discussed with respect to FIG. 5A. Reflective layer may be built into a flexible PCB. In another example, the housing 504 can be made from opaque material to prevent the light signals 540 and 546 from reaching the detector units 530b and 530c, respectively. FoV of the emitter unit 530a and/or the detector units 530b and 530c can be redesigned. FIGS. 5B and 5C illustrate concept of narrowing FoV according to an embodiment of the present disclosure. Overlapping FoV between emitter units and detector units can introduce errors in measurement. In FIG. 5B, a receiver-in-canal block diagram 564 contains an emitter unit 562 that produces a wide beam 560a. The emitter unit 562 can be designed to narrow the wide beam 560a to a narrow beam 560b which does not overlap with a FoV of another emitter unit or detector unit. In FIG. 5C, a receiver-in-canal block diagram 566 includes an emitter unit and a detector unit on a same side. The emitter unit and the detector unit have wide FoV indicated by the wide beams 568a and 570a. The emitter unit and the detector unit FoV can be adjusted to 568b and 570b, respectively, using some embodiments of the present disclosure.

Figure 6:
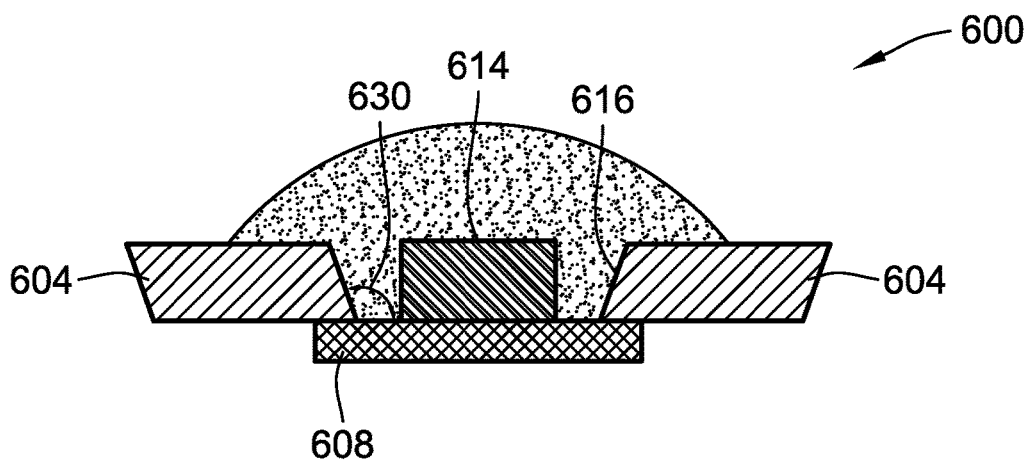
FIG. 6 illustrates a cavity within a housing of a receiver-in-canal assembly with slanted sidewalls according to an embodiment of the present disclosure.
Figure 7:
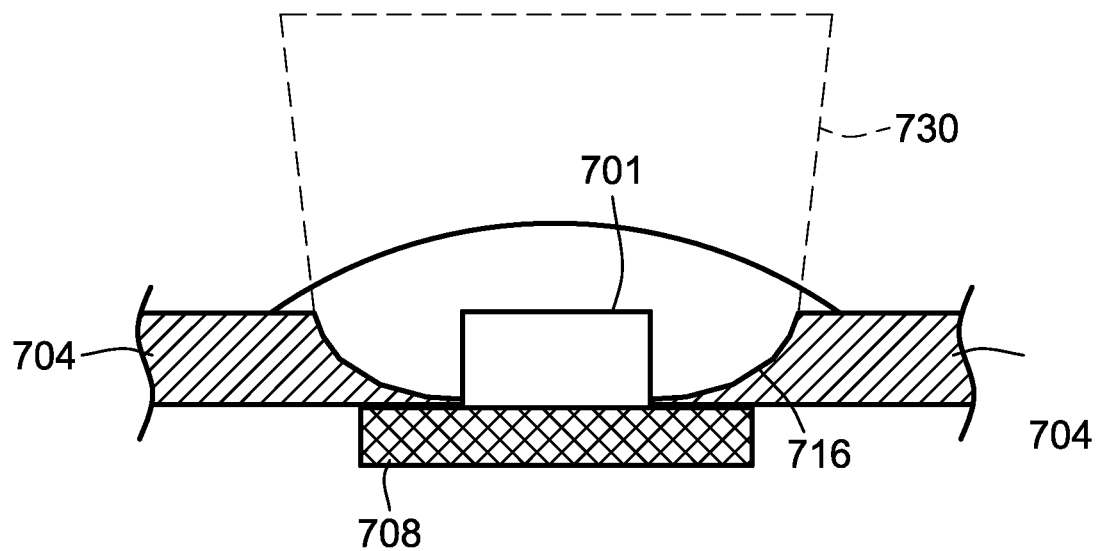
FIG. 7 illustrates a cavity within a housing of a receiver-in-canal assembly with parabolic sidewalls according to an embodiment of the present disclosure.

FIGS. 6 and 7 illustrate designs of cavities for reducing FoV according to some embodiments of the disclosure. In FIG. 6, the cavity in a housing 604 includes slanted sidewalls 616. The sidewalls can be slanted at an angle 630 with respect to a circuit board layer 608. The angle 630 can be at least 90 degrees such that signals reflecting from the slanted sidewalls 616 are directed toward a center axis of the cavity. In embodiments where the radiating element 614 is an active region of an LED, having slanted sidewalls 616 increase luminosity around the center axis of the cavity. The slanted sidewalls 616 can include deposits of reflecting material to increase amount of light reflected.

FIG. 6 also incorporates a new design for the emitter when compared to FIG. 2C. The emitter 201 in FIG. 2 includes the ceramic base 218 and the clear LED coating 202. In FIG. 6, the emitter can be made smaller by not including a ceramic base, and the active substance (the radiating element 614) can be bonded directly to the circuit board layer 608. An example dimensions for the radiating element 614 is 0.22 mm length by 0.22 mm width by 0.15 mm height. Manufacturing can be simplified by using one protective substance to fill the cavity rather than having a clear LED coating underneath the protective substance. An advantage of removing the ceramic base from the emitter is that the housing 604 can be made thinner since a height of the radiative element 614 is lower than a combined height of a radiative element and a ceramic base.

Referring to FIG. 7, a cavity with parabolic walls 716 in a housing 704 is provided. FIG. 7 includes an emitter 701 for emitting signals that travel in a FoV indicated by item 730. Similar to FIG. 2C, the emitter 701 can sit on a circuit board layer 708. Signal beams from the emitter 701 are narrower due to the parabolic walls 716.

Figure 8:
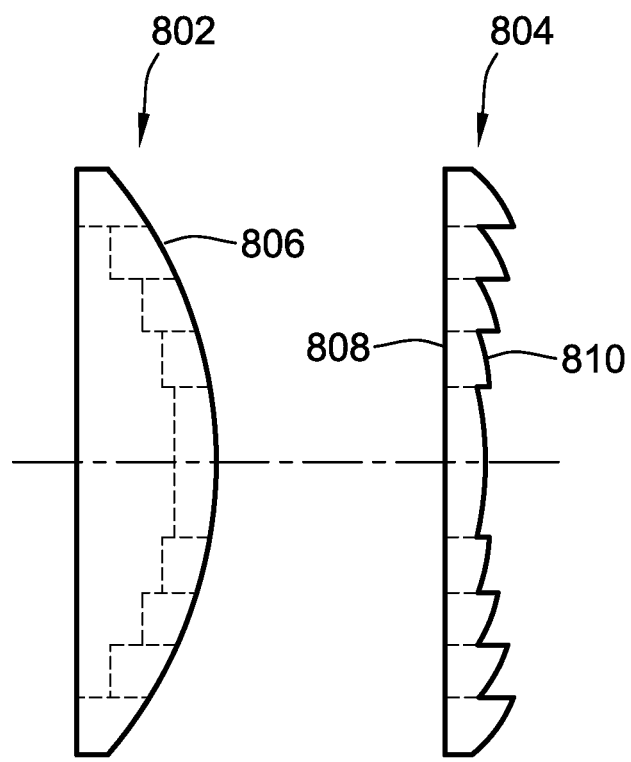
FIG. 8 illustrates an example of a Fresnel lens for beam shaping according to an embodiment of the present disclosure.

Narrower beams can also be obtained via the shaping of a top boundary of a protective substance, e.g., the protective substance 210. Shaping of the top boundary can be achieved, for example, by adding a lens on top (or inside) a glue of the protective substance, or by pressing a shape of a lens into the glue while the glue is solidifying. The protective substance 210 is dome-shaped. For example, glue can be deposited as the protective substance 210, and once the glue solidifies, it retains the dome shape. In some embodiments, a Fresnel lens according to FIG. 8 can be used to obtain a flat surface instead of a dome-shaped top boundary. FIG. 8 illustrates a dome-shaped lens 802 according to embodiments of the present disclosure with a top surface 806. A dome-shaped lens 802 can be used in instead-of or in-addition to the protective substance 210. Alternatively, a transparent window (e.g., in the form of flat lens or a Fresnel lens 804) can be used to cap a cavity in a housing of a receiver-in-canal assembly containing an emitter or a detector. An outer surface 808 of the Fresnel lens can take on a flat shape, parallel to that of the emitter, e.g., the emitter 201. An inner surface 810 interfacing with the protective substance can be patterned to encourage narrower signal beams.

In some embodiments, a lens is used to cover or cap a cavity in a housing of a receiver-in-canal assembly containing an optical transducer. The capped cavity can be filled with a sealing glue to environmentally protect the inside of the cavity. Preferably, the capped cavity is filled with clear or transparent glue, epoxy, or adhesive for optimal optical coupling of the lens to the optical transducer. Also preferably, a volume between sides of the optical transducer (e.g., the clear LED coating 220) and the housing are filled with clear or transparent glue, epoxy, or adhesive, touching sides of the optical transducer without air bubbles, for optimal optical coupling of the lens to the sides of the optical transducer. The filling up of the volume at the sides of the transducer may be the preferred design not only when there is a lens on top, but also to optimize the coupling of the transducer to the outside of the device.

Figure 9A:
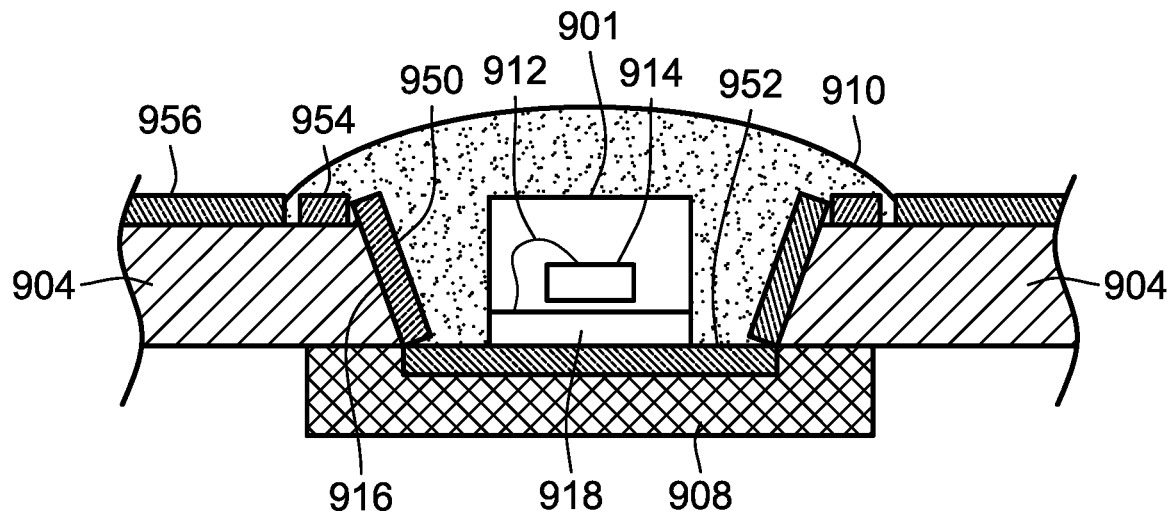
FIGS. 9A, 9B, and 9C illustrate example areas to have reflective surfaces according to an embodiment of the present disclosure.
Figure 9B:
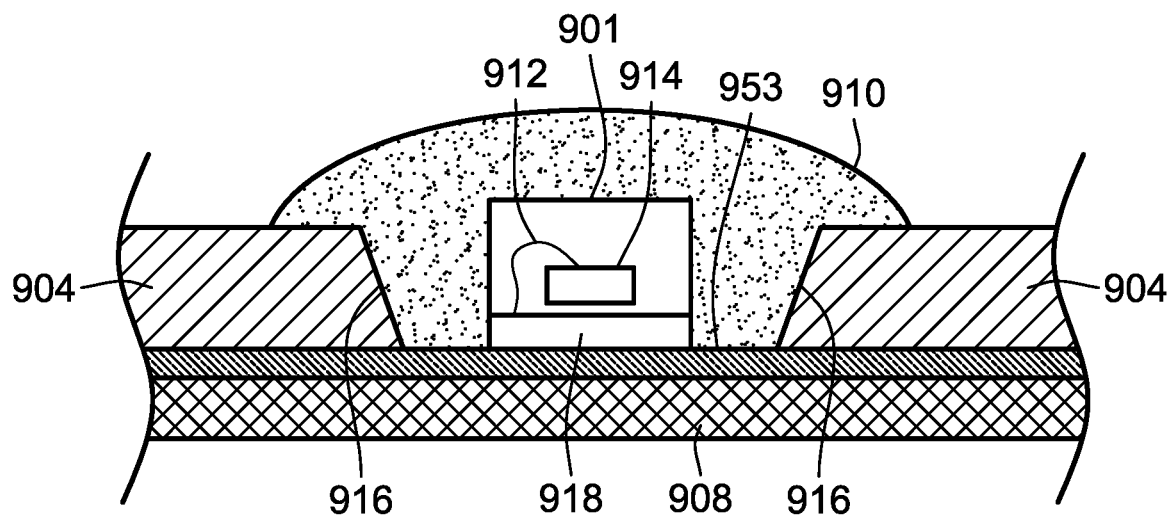

To further prevent emitted signals from penetrating the housing, one or more reflective surfaces or reflectors can be provided as depicted in FIGS. 9A and 9B. A reflective surface is a surface that reflects incident light that reaches the surface. For example, a surface can be classified as a reflective surface if more than 50% of incident light is reflected, if more than 75% of incident light is reflected, if more than 90% of incident light is reflected, or if more than 99% of incident light is reflected. FIG. 9A illustrates an emitter location within a cavity of a housing 904 of a receiver-in-canal assembly according to an embodiment of the present disclosure. The cavity is shown to have slanted sidewalls 916. Within the cavity is an emitter 901 with a radiating element 914 on a ceramic base 918. The radiating element 914 is connected to a circuit board layer 908 via a wire 912. A protective cover 910 is provided according to embodiments of the present disclosure.

A reflective surface 952 can be provided in the cavity. The reflective surface 952 may not extend under the housing 904. In some embodiments, a reflective surface 953 (as shown in FIG. 9B) can be provided that extend under the housing 904. The slanted sidewalls 916 can have reflective surface 950. An area of the housing 904 covered by the protective substance 910 can have a reflective substance 954 between the housing 904 and the protective substance 910. An area of the housing not covered by the protective substance 910 can have a reflective substance 956 covering the housing 904.

In some embodiments, the reflective substance 956 is used sparingly whereby the reflective substance 956 is positioned at areas of the housing near the emitter 901 and/or areas of the housing near a detector. In some embodiments, the reflective substance 956 can be used anywhere on the housing and not limited to areas proximate to an emitter or a detector.

Using reflective substances according to embodiments of the disclosure allow the housing 904 in FIGS. 9A and 9B to be, at least partly, made from clear material. The remainder of the housing 904 not made from clear material can be made from opaque material to obtain relatively higher bifurcation between an emitter and a detector, minimizing light from the emitter reaching the detector through the housing without interfering with the ear canal tissue of the user (see e.g., the light signals 540 and 546 of FIG. 5A) and/or to obtain shielding of the detector from ambient light or other disturbing light sources. In some embodiments, the reflective substance is a metal deposit, e.g., a copper deposit. By having a conductive material as a reflective surface and having the conductive material connected to an electrical circuit or an electrical ground, the conductive material can function as an electromagnetic interference (EMI) shield or a capacitive sensing element. In some implementations, metallic layers of the circuit board layer 908 are used as both a reflective surface and an EMI shield.

Reflective surfaces according to some embodiments can be formed by coating a surface with a reflective coating. Reflective surfaces can be plastic of reflective color for a respective light wavelength, plastic with reflective particles, metal, etc. Using reflective surfaces and substances according to embodiments of the present disclosure provides several advantages. Reflective surfaces prevent light from entering the housing of the receiver-in-canal hearing aid device. Thus, there is no loss associated with absorbing light within the housing or contributing to measurement errors as described with respect to the light signal 546 in FIG. 5A. Reflective surfaces, when added to sidewalls, can increase light intensity by 10 to 20 percent. Reflective surfaces can thus be used to promote focused beams and/or concentrated light. Concentrated light can be beneficial in obtaining biometric data from specific locations in the ear of a patient. Concentrated light improves bifurcation by ensuring that light is not traveling from emitter directly to detector without interacting with tissue in the ear.

In emitters that support multiple wavelengths, reflective surfaces can be used to direct light of different wavelengths in different directions. This can be beneficial because different wavelengths can be targeted to different areas within the ear canal to measure signals at specific locations simultaneously. In some embodiments, reflective surfaces being used within the housing of the receiver-in-canal assembly enables higher measurement efficiency compared to those without reflective surfaces. LEDs with reflectors are too large to fit on small receiver-in-canal assemblies. As such, embodiments of the disclosure provide a design that can be adapted to placement on small receiver-in-canal assemblies. Transparent and/or translucent materials embedded in or for use in, e.g., a transparent housing, glue, sealants, lenses, windows, etc., can have additional optical properties. For example, these materials can form an optical filter to filter out certain wavelengths. In an example, transparent and/or translucent material can filter out ambient light such that the ambient light does not reach a detector.

Since detectors cannot be provided on every square millimetre of a receiver-in-canal assembly, reflective surfaces covering a housing of the receiver-in-canal assembly can guide light signals coming from the ear canal to a detector provided on the housing of the receiver-in-canal assembly. The light signals can bounce back and forth between the reflective surface and the ear canal until they reach a detector.

Figure 9C:
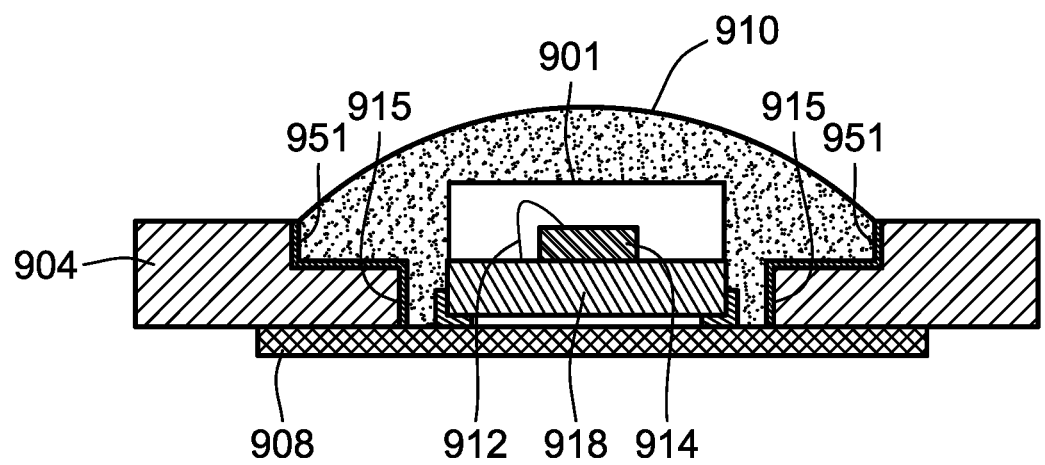

FIG. 9C illustrates an example of adding reflective surfaces 951 on stepped sidewalls 915. The stepped sidewalls 915 are shown to only include one step, but in other embodiments, the sidewalls can include more than one step and the present disclosure is not limiting a number of steps of the sidewalls. Although the reflective surfaces 951 are added to the stepped sidewalls 915, other embodiments can be shown where the reflective surfaces 951 are not included.

Figure 9D:
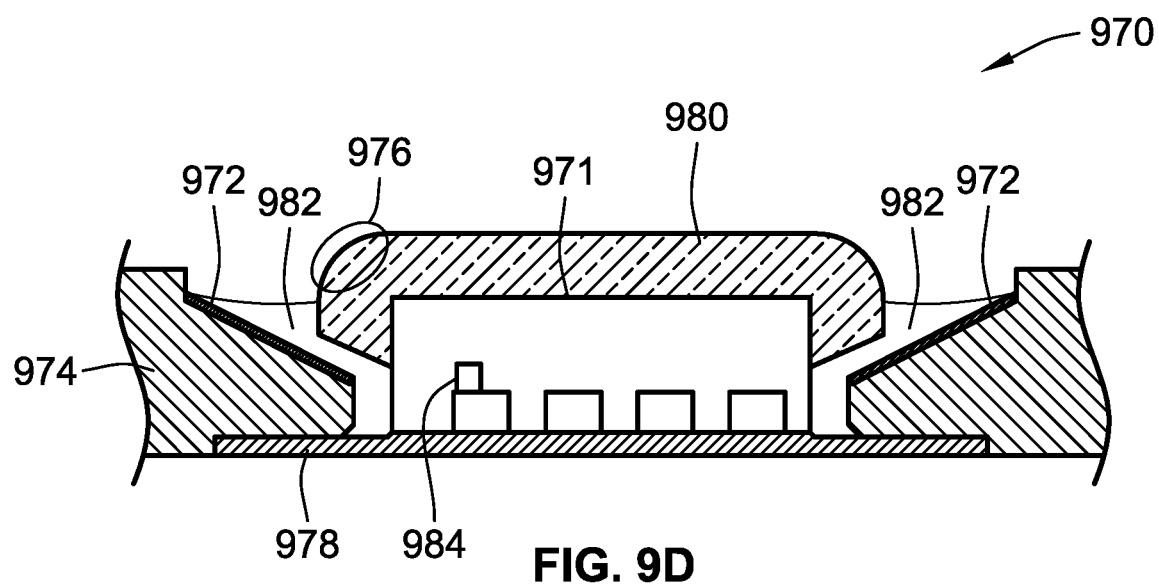
FIG. 9D illustrates an example of adding reflective surfaces to improve detector efficiency according to an embodiment of the present disclosure.

FIG. 9D illustrates an example of adding reflective surfaces 972 to a cavity 970 including a detector 971, according to an embodiment of the present disclosure. The cavity 970 is formed in a housing 974 of a receiver-in-canal assembly. The detector 971 can be covered by a window 980 and can be coupled to a circuit board layer 978. The detector can include an active sensing element 984. The window 980 can be a sunlight filtering window that filters out ambient light. The window 980 can have a rounded corner 976 for improving FoV of the detector 971. Empty space in the cavity 970 can be filled with glue 982 to hold the window 980 and the detector 971 in place. In some embodiments, reflective surfaces 972 can be added to improve efficiency of light sensed by the detector 971.

Figure 10A:
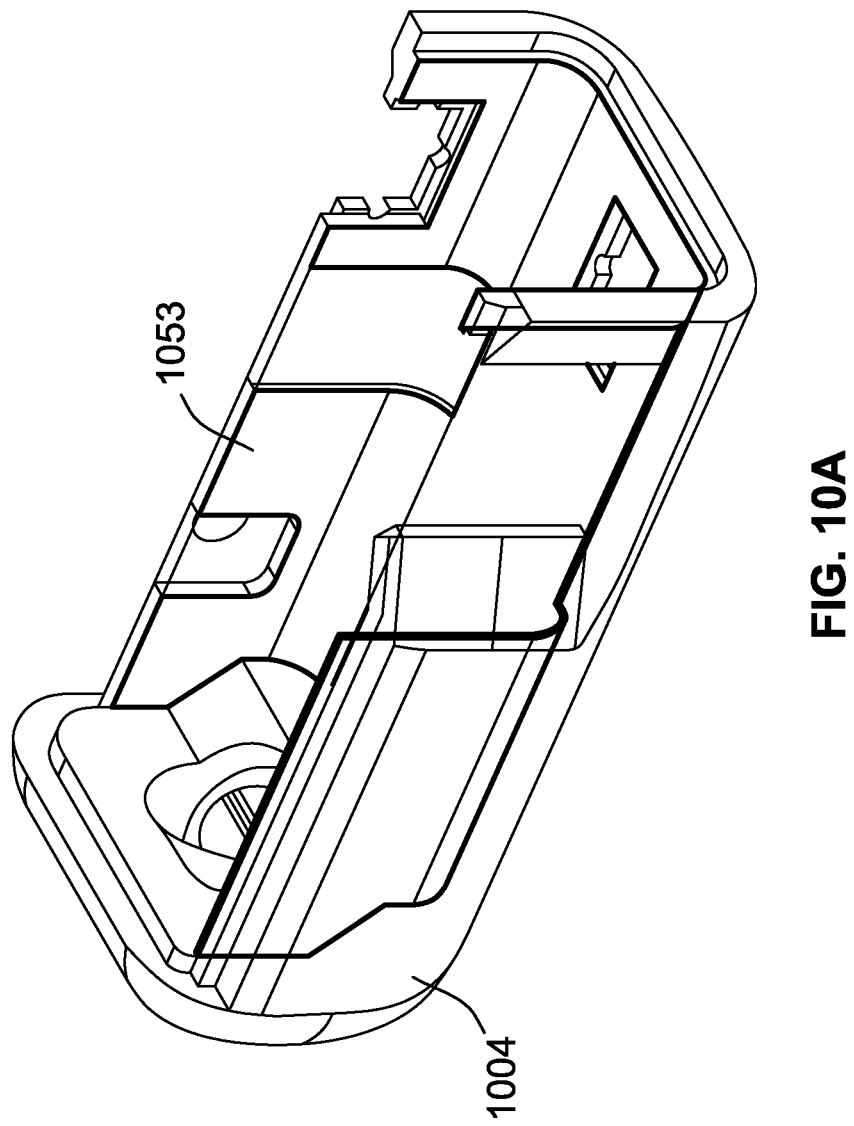
FIG. 10A illustrates a reflective surface installation in a housing according to an embodiment of the present disclosure.

FIG. 10A illustrates a reflective surface 1053 installed in a transparent housing 1004 of a receiver-in-canal assembly according to an embodiment of the present disclosure. The reflective surface 1053 can be achieved by folding or wrapping a reflective foil or layer on an inside of the transparent housing 1004. The reflective layer could be omitted in spots where there are other reflective components present, like e.g. the receiver housing.

FIGS. 11A, 11B, and 11C illustrate examples of using reflectors to reduce separation between emitters and detectors according to some embodiments of the present disclosure. Referring to FIG. 11A, an emitter unit 1130a is separated from a detector unit 1130b by a thin wall 1104 with reflectors 1134a and 1134b on each side of the thin wall 1104.

Referring to FIG. 11B, an emitter unit 1130c is separated from a detector unit 1130d by a reflector 1136. Since the reflector 1136 is only one reflector, the emitter unit 1130c can be placed closer to the detector unit 1130d when compared to the emitter and detector units of FIG. 11A. Empty spaces in the emitter unit 1130c and the detector unit 1130d can be filled with transparent glue 1137. Referring to FIG. 11C, an emitter unit 1130f and a detector unit 1130e can be placed very close to each other and only separated by a reflector 1138. The emitter units and detector units of FIGS. 11A-11C can be built on edges of receiver-in-canal assemblies. In comparison to FIG. 5A, use of reflectors in FIGS. 11A and 11B eliminate noise effects of the light signal 546 thus allowing more compact placement of emitter and detector units. In comparison to FIG. 5A, the reflector 1138 eliminates noise effects of the light signal 540 thus allowing more compact placement of emitter and detector units.

It should be noted that the transducers in FIG. 11A may be covered by transparent glue only, as protective layer, and that the transducers in FIG. 11B may be covered by, at least, moulded windows and, preferably, glue between the windows and the emitter.

Figure 12A:
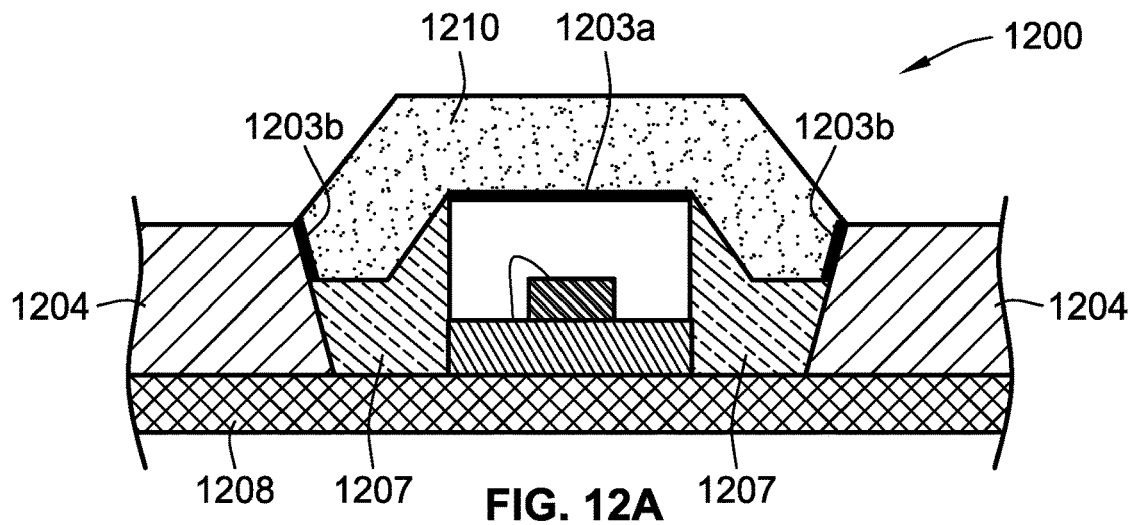
FIG. 12A illustrates shielding a cavity with a premolded window according to an embodiment of the present disclosure.

FIG. 12A illustrates shielding a cavity 1200 including an emitter with a premolded window 1210 according to an embodiment of the present disclosure. The premolded window 1210 can be a lens as previously described. The emitter is mounted on a circuit board layer 1208 in the cavity 1200 created within the housing 1204 of a receiver-in-canal assembly. The premolded window 1210 can include one or more glues 1203a, 1203b, .... The glues 1203b can be environmental sealing glue, and the glue 1203a can provide optical properties for guiding light from the emitter through the premolded window 1210. Empty spaces within the cavity can be filled with transparent glue 1207 such that there is no air flowing from within the cavity to the environment outside the cavity and/or such that there is an optimal optical coupling between transducer and the outside world.

Figure 12B:
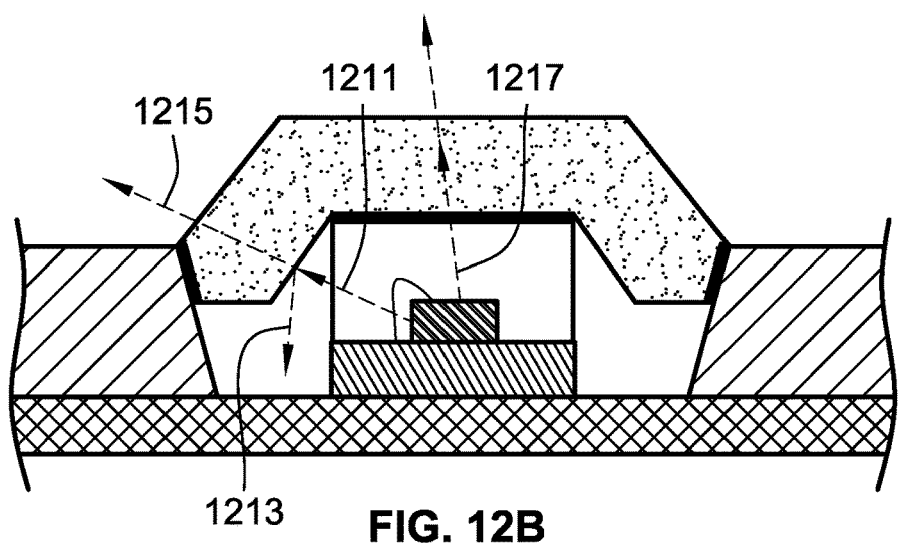
FIGS. 12B and 12C illustrate light ray tracings according to some embodiments of the present disclosure.
Figure 12C:
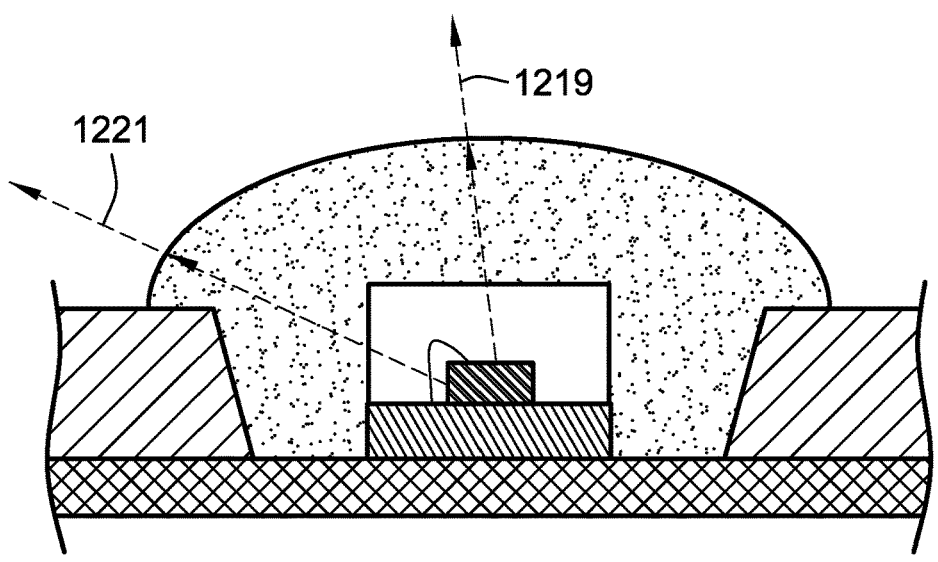

FIGS. 12B and 12C illustrate light ray tracings of different emitter units according to some embodiments of the present disclosure. Referring to FIG. 12B, an emitter emits light that travels in directions indicated by rays 1217 and 1211. Light can reflect when hitting a boundary or when flowing from one medium to another. As such, some light from the ray 1211 can be reflected as 1213 and some can be passed as 1215. Light intensity lost due to the reflection can be about two to six percent. In comparison, FIG. 12C shows no reflections as rays 1219 and 1221 follow a same trajectory as emitted from the emitter. Placing glue 1207 as in FIG. 12A will minimize reflections 1213.

Figure 12D:
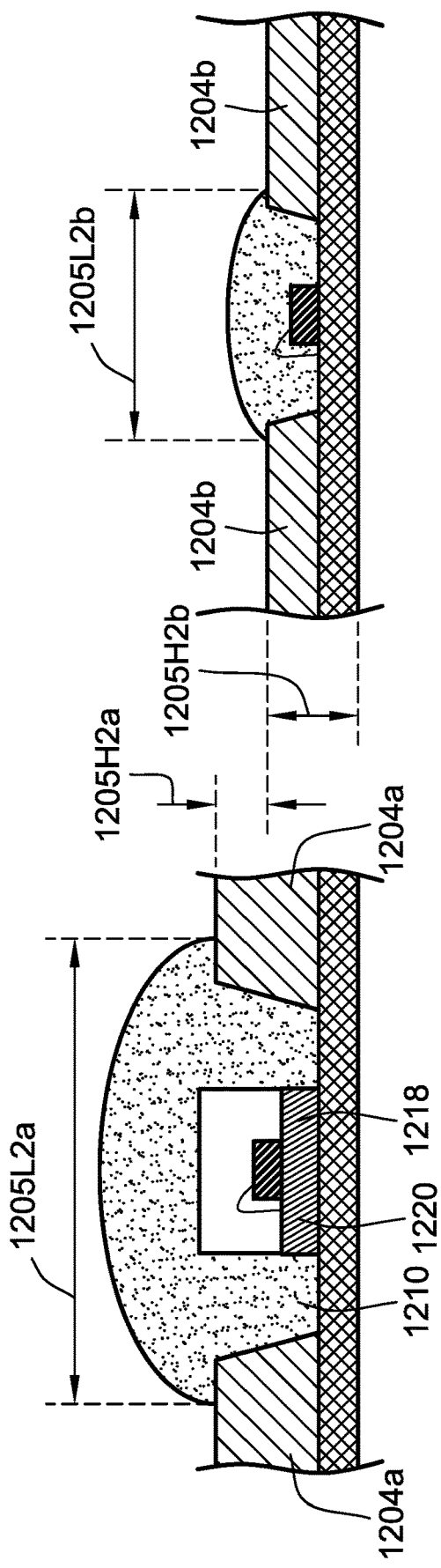
FIG. 12D compares dimensions of two cavities including two different emitters according to some embodiments of the present disclosure.

FIG. 12D compares dimensions of two cavities including two different emitters according to some embodiments of the present disclosure. A first emitter has a ceramic base 1218 and a clear LED coating 1220 and is situated between housing 1204a. A protective substance 1210 covers the first emitter. A second emitter does not have a ceramic base or a clear LED coating (similar to the emitter in FIG. 6) and is situated between housing 1204b. As a result, the housing 1204b can be made thinner than the housing 1204a, and less material can be used as a protective substance for the second emitter compared to the protective substance 1210. In FIG. 12D, length 1205L2a is larger than length 1205L2b, and height 1205H2a is larger than height 1205H2b.

Figure 12E:
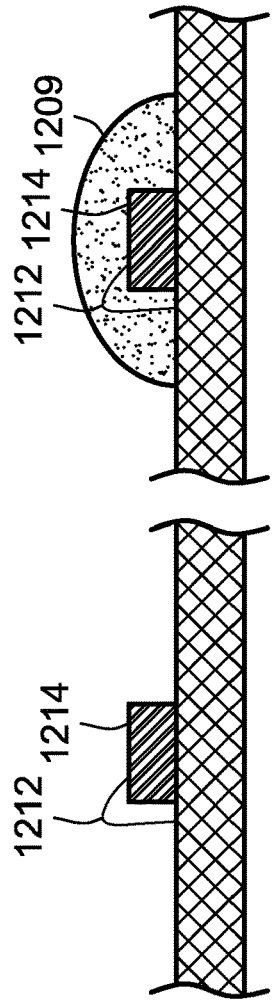
FIG. 12E illustrates two types of emitters according to an embodiment of the present disclosure.

FIG. 12E illustrates two types of emitters according to an embodiment of the present disclosure. The first type of emitter can have only an active element 1214 and a wire 1212. The second type of emitter can have in addition to the active element 1214 and the wire 1212, a clear coating 1209. The second type of emitter being pre-covered with the clear coating 1209 is more resilient to damage of the wire 1212 when mounting the second type of emitter in a housing of a receiver-in-canal assembly.

Figure 13A:
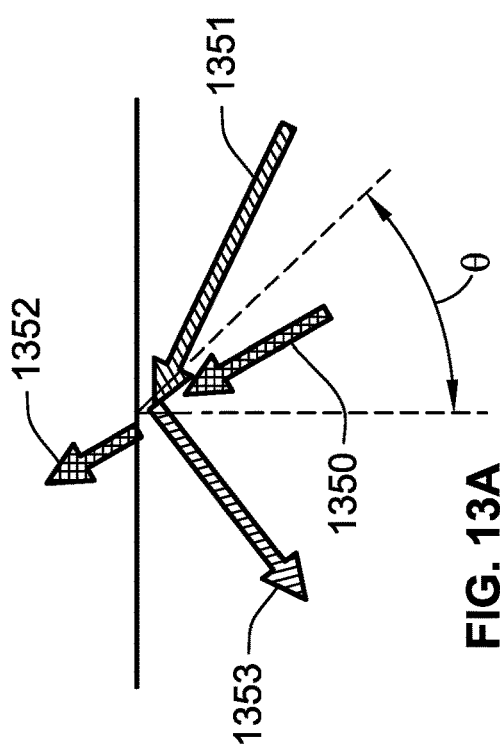
FIG. 13A illustrates a concept of a critical angle according to an embodiment of the present disclosure.

FIG. 13A illustrates a concept of a critical angle according to an embodiment of the present disclosure. When light is traveling from a first medium to a second medium and its angle of incidence at a boundary between the two media is greater than a critical angle $\theta$, then a refracted ray will not emerge in the second medium. For example, light ray 1350 has an angle of incidence less than the critical angle $\theta$, so refracted ray 1352 emerges. Light ray 1351 has an angle of incidence greater than the critical angle $\theta$, so it reflects at the boundary as reflected ray 1353.

Figure 13B:
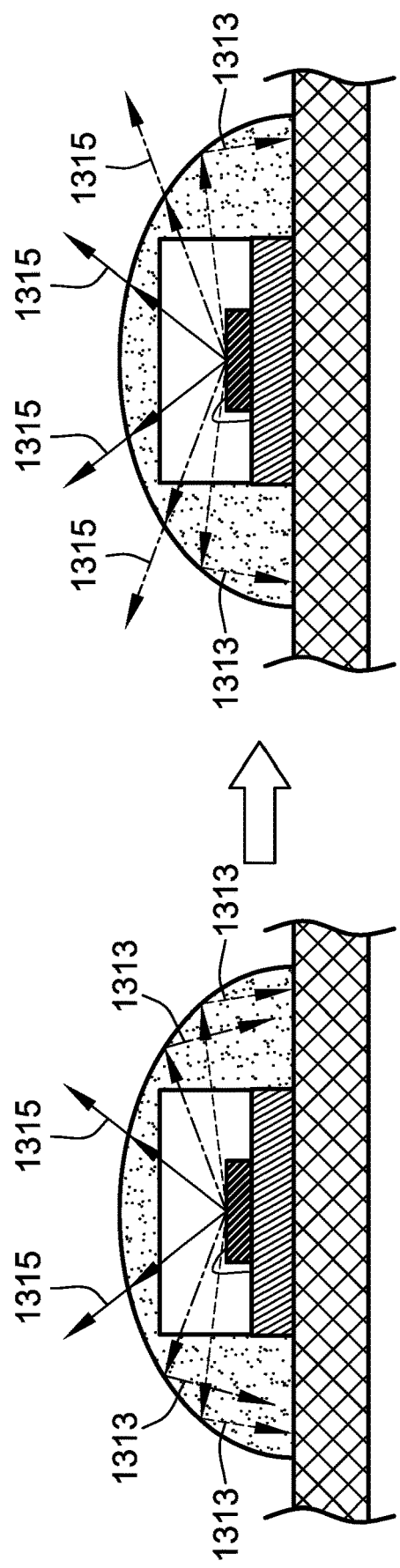
FIGS. 13B and 13C illustrate light ray tracings according to some embodiments of the present disclosure.
Figure 13C:
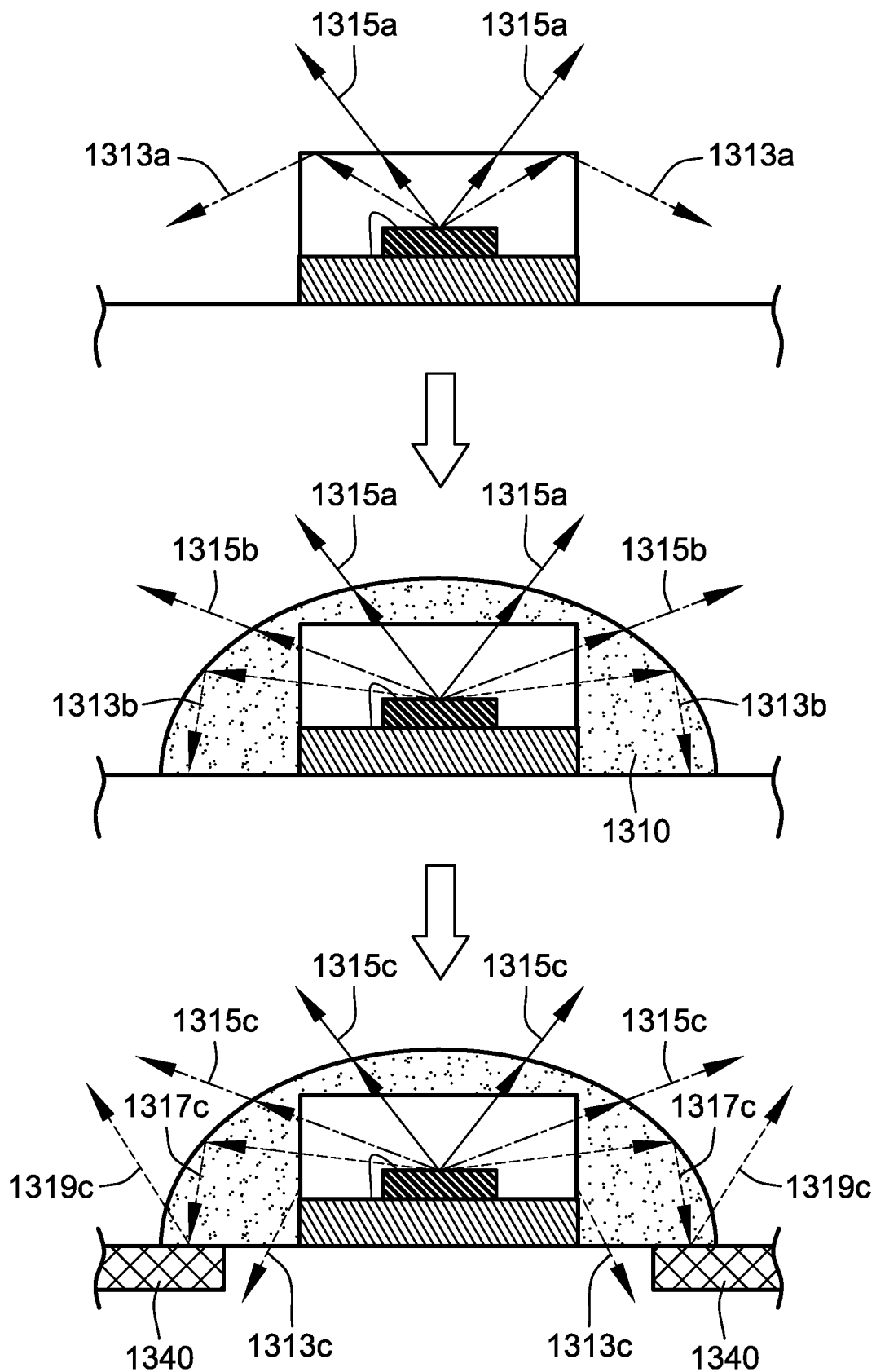

FIGS. 13B and 13C illustrate light ray tracings according to some embodiments of the present disclosure. Referring to FIG. 13B, curvature of a protective layer can influence light escaping from an emitter. In FIG. 13B, the emitter on the left is under a protective layer that has a larger curvature compared to the protective layer covering the emitter on the right. As such, more light rays 1315 escape the protective layer for the emitter on the right compared to the emitter on the left. Thus, more light rays 1313 are reflected at the protective layer for the emitter on the left compared to the emitter on the right.

Referring to FIG. 13B, one of the ways to change the curvature radius may be to select a corresponding material.

Referring to FIG. 13C, light efficiency for light escaping the emitter can be increased by using reflectors. Three designs, a first design without a protective layer, a second design with a protective layer 1310, and a third design with a protective layer 1310 and reflectors 1340 are provided. In the first design, light rays 1313a are reflected and will eventually be absorbed by a housing while light rays 1315a escape. In the second design light rays 1313*b* are reflected and will eventually be absorbed by the housing while light rays 1315*b* escape. In the third design light rays 1317*c* are reflected by the protective layer but then captured and reflected by the reflectors 1340 as light rays 1319*c*. As such, light rays 1315*c* and 1319*c* escape while light rays 1313*c* are captured. When comparing brightness of the three designs, the second design can be five percent brighter than the first design, and the third design can be twenty-three percent brighter than the first design.

Figure 13E:
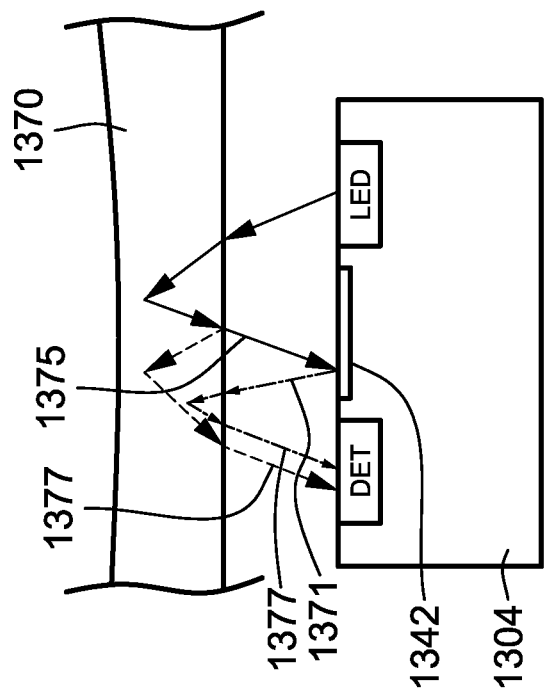
FIG. 13E illustrates light ray tracings for a housing with a reflective surface according to some embodiments of the present disclosure.
Figure 13D:
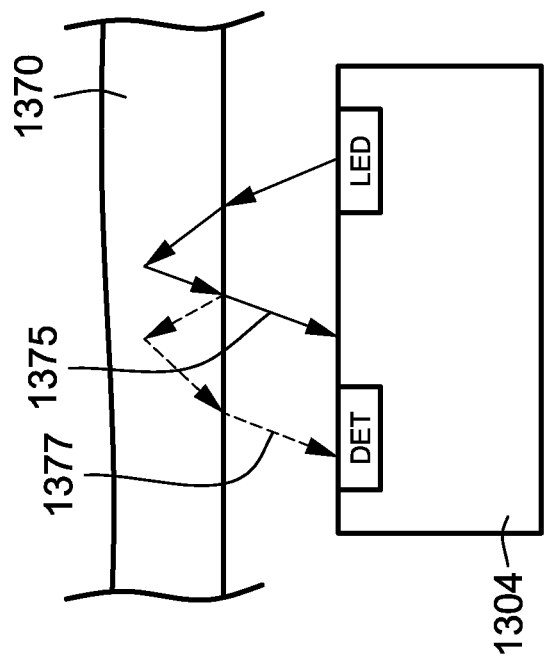
FIG. 13D illustrates light ray tracings for a housing without a reflective surface according to some embodiments of the present disclosure.

FIG. 13D illustrates light ray tracings for a housing 1304 according to some embodiments of the present disclosure. Light from an emitter in a cavity of the housing 1304 hits an ear canal wall 1370 and can bounce around in the ear canal wall 1370, picking up biometric signals. The light can then exit the ear canal wall 1370 as light rays 1375 and 1377. The light ray 1375 misses the detector and is absorbed by the housing 1304 while the light ray 1377 is sensed by the detector.

FIG. 13E illustrates light ray tracings for a housing 1304 with a reflective surface 1342 according to some embodiments of the present disclosure. Similar situation as FIG. 13D above except the reflective surface 1342 prevents light ray 1373 from being absorbed by the housing 1304. Instead the light ray 1373 is reflected as light ray 1371, further picking up biometric signals in the ear canal wall 1370 before returning to the detector as part of the light ray 1377.

In some embodiments, a goal is to reflect light of wavelengths used by a PPG sensor (e.g., wavelengths at near infrared 850 nm, green or red). Minimum reflectance can be about 30 to 40 percent, acceptable reflectance can be 75 percent, good reflectance can be about 90 percent, and excellent reflectance can be above 97 percent. Thickness of any layer or housing material can be determined by an amount of light reflected from the layer, therefore, a minimum thickness of any layer can be set based on light reflected from the material. For example, 50 percent reflectivity can be set as a minimum with 90 percent set as ideal. Material thickness for the housing can then be designed to achieve desired reflectivity. Maximum thickness of material can be determined based on design, production limitations, and cost limitations. Examples of these limitations may include fitting rate of a hearing aid device in the ear canal, being able to bend a metallic part, cost of evaporating gold, etc.

For example, the layer thickness may be:
metal (e.g. gold): ~50 nm;
paint/ink: ~10-50 μm;
for plastics, the thickness may be dependent on material and filler. Often, the plastic thickness is determined by maximum build size, and plastic is usually partly transparent for our common wall thicknesses of 0.2 mm or 0.35 mm (for small and large features respectively).

Figure 14A:
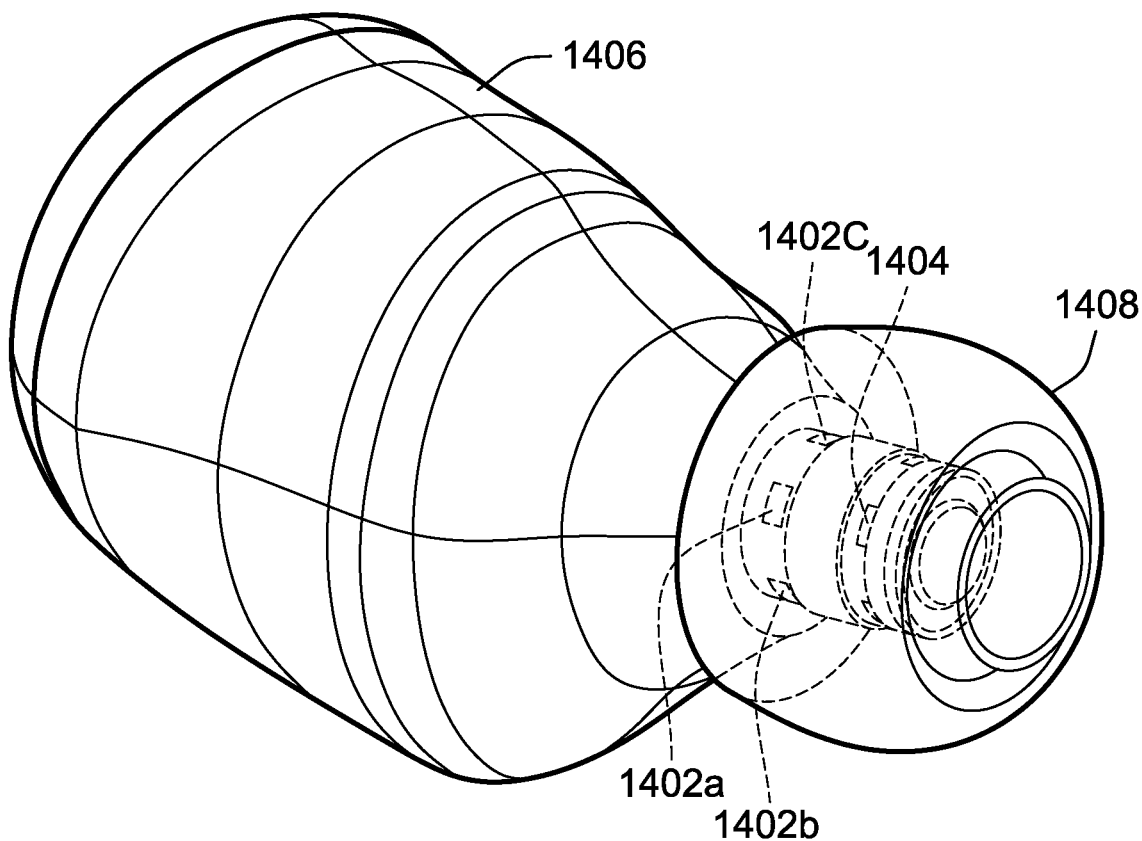
FIG. 14A illustrates a perspective view of an earbud with optical sensors according to some embodiments of the present disclosure.
Figure 14B:
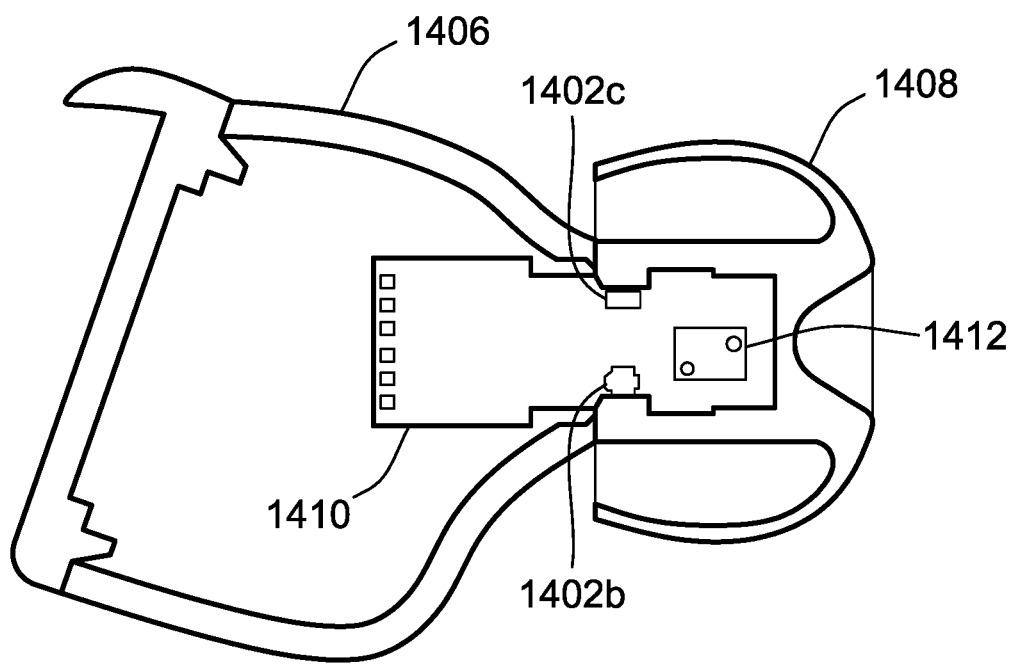
FIG. 14B illustrates a cross-sectional view of the earbud in FIG. 14A.

Embodiments of the disclosure can not only be used in hearing aid devices but can be incorporated in earbuds. FIG. 14A illustrates a perspective view of an earbud 1400 with optical sensors according to some embodiments of the present disclosure. The earbud 1400 can include a transparent dome 1408, a housing 1406, and one or more emitters positioned along a nozzle of the earbud 1400. Items 1402*a*, 1402*b*, 1402*c* represent transparent windows where emitters emit light, and item 1404 represents a transparent window for a detector to collect light. FIG. 14B illustrates a cross-sectional view of the earbud 1400 in FIG. 14A. The earbud 1400 can include a flexible circuit board 1410 connected to emitters and a detector 1412.

Figure 15A:
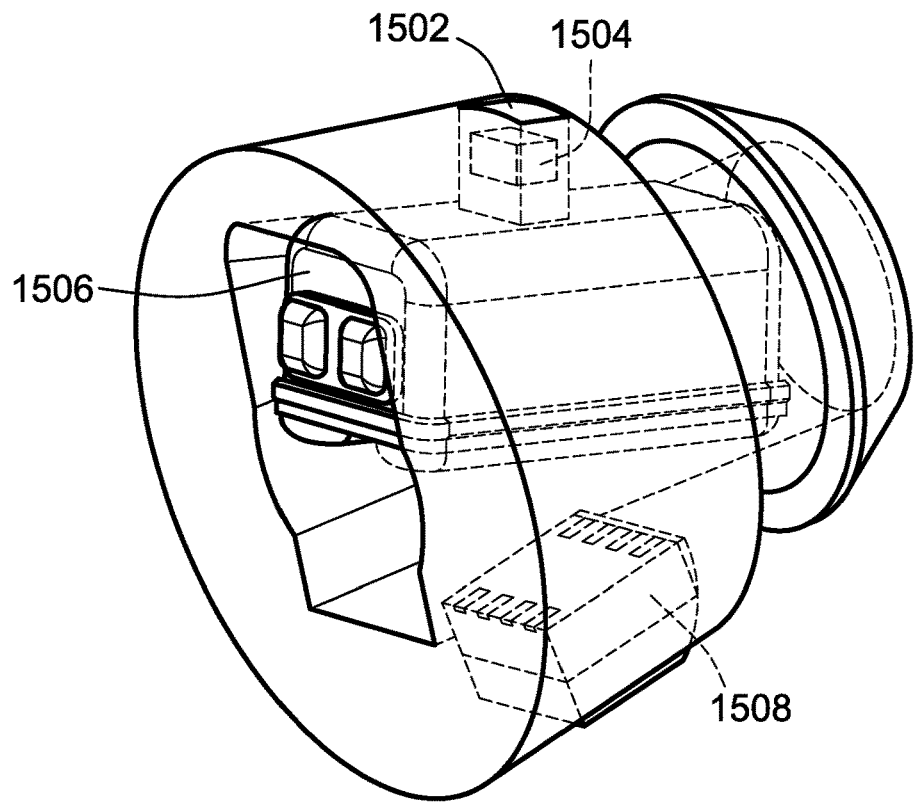
FIG. 15A illustrates a perspective view of an earbud nozzle with optical sensors according to some embodiments of the present disclosure.
Figure 15B:
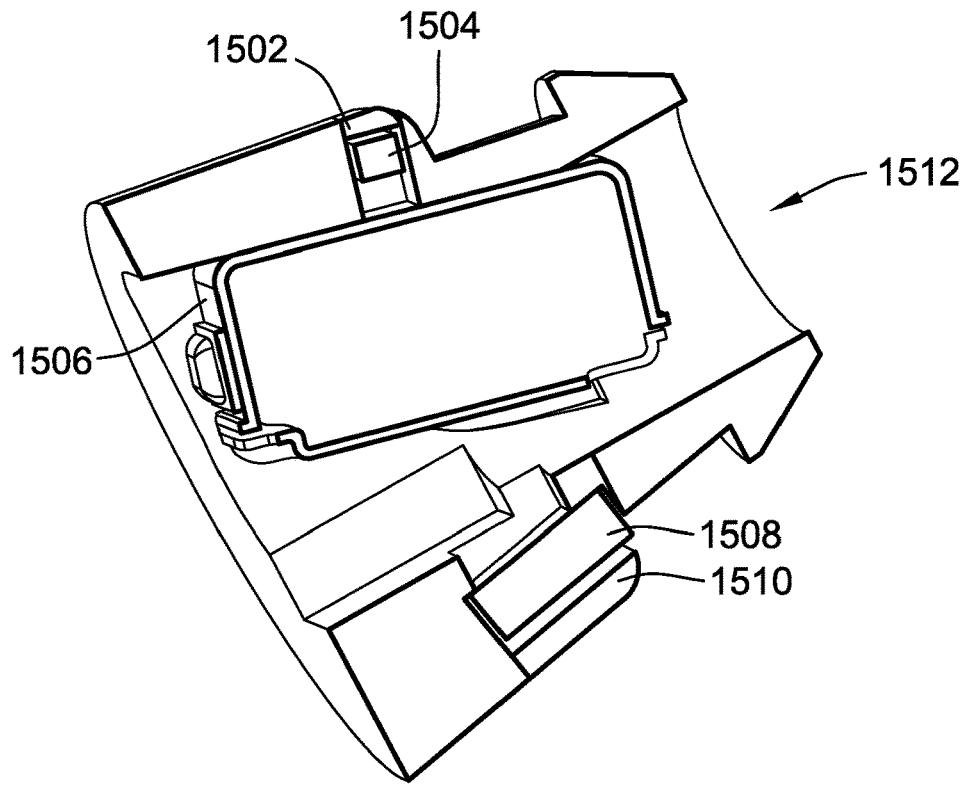
FIG. 15B illustrates a cross-sectional view of the earbud nozzle in FIG. 15A

FIG. 15A illustrates a perspective view of an earbud nozzle with optical sensors according to some embodiments of the present disclosure. The earbud nozzle can replace the earbud nozzle of FIG. 14A. FIG. 15B illustrates a cross-sectional view of the earbud nozzle in FIG. 15A. The earbud nozzle in FIG. 15A has a thick housing with a transparent window 1502, an emitter 1504, a detector 1508, and a window 1510 for the detector 1508. A speaker 1506 can be provided in the earbud nozzle for providing sound that travels through a sound channel 1512.

FIG. 16A illustrates a cross-sectional view of an earbud 1600 with optical sensors according to some embodiments of the present disclosure. The earbud 1600 includes a nozzle 1614 holding a flexible circuit board 1620 and a speaker/receiver 1606. FIG. 16B illustrates a cross-sectional view of electronic components of the earbud 1600 of FIG. 16A. An emitter 1604 is provided on the flexible circuit board 1620. A detector 1608 is provided on the flexible circuit board 1620. A spacing can exist between the emitter 1604 and the housing of the nozzle 1614. FIG. 16C illustrates an embodiment of the spacing between the emitter 1604 and a window 1602 of FIG. 16B. The spacing can be filled with a light guide 1605. The light guide 1605 can be, for example, glue, plastic, air, etc. FIG. 16D illustrates the nozzle 1614 and electronic components of the nozzle 1614 of FIG. 16A-16B. The nozzle 1614 can have guides that allow the flexible circuit board 1620 to slide into the nozzle 1614.

Figure 17A:
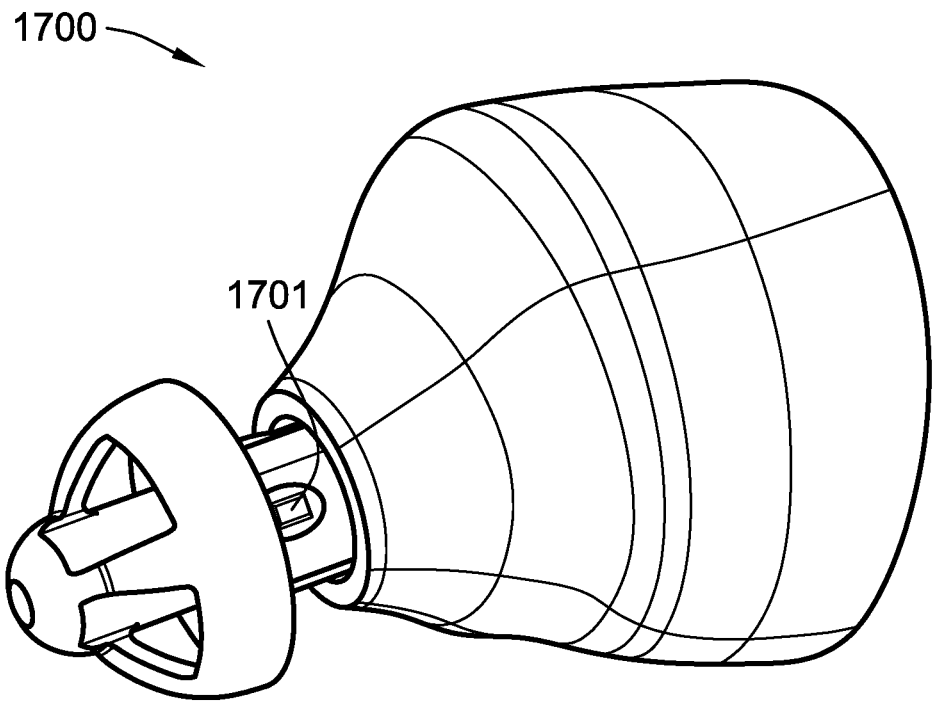
FIG. 17A illustrates a perspective view of an earbud with optical sensors according to some embodiments of the present disclosure.
Figure 17B:
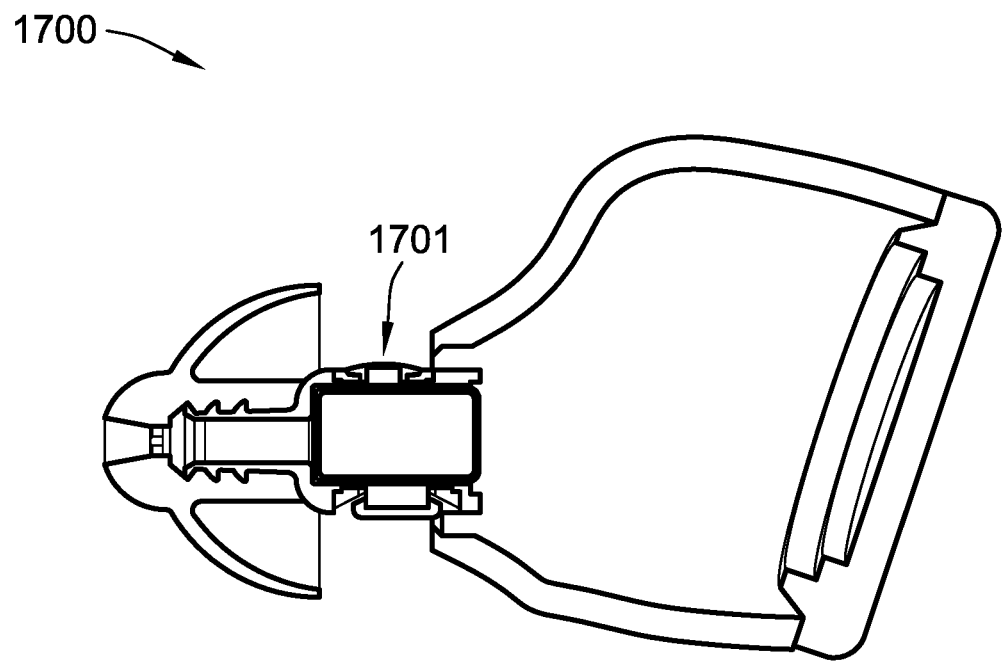
FIG. 17B illustrates a cross-sectional view of the earbud in FIG. 17A.

FIG. 17A illustrates a perspective view of an earbud 1700 with optical sensors according to some embodiments of the present disclosure. FIG. 17B illustrates a cross-sectional view of the earbud 1700 in FIG. 17A. The earbud 1700 includes a single dome, and an emitter can be placed at location 1701.

Figure 18A:
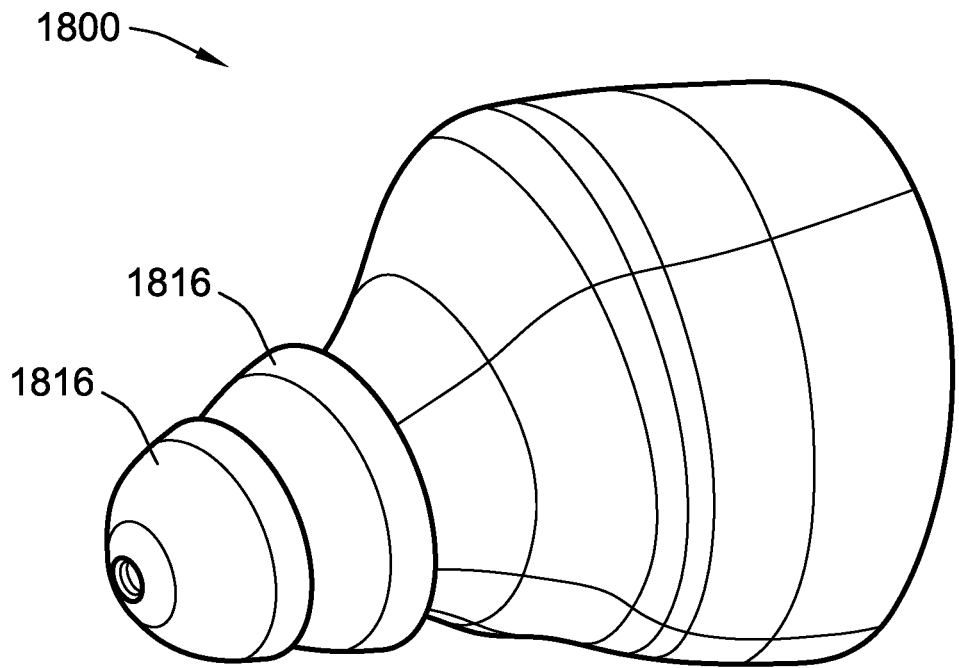
FIG. 18A illustrates a perspective view of an earbud with optical sensors according to some embodiments of the present disclosure.
Figure 18B:
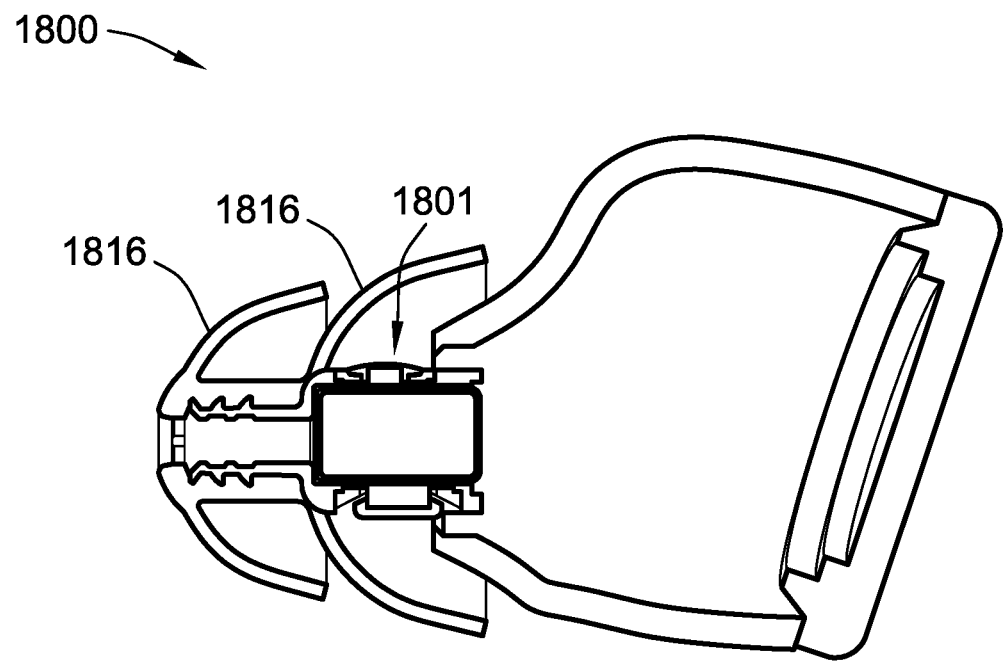
FIG. 18B illustrates a cross-sectional view of the earbud in FIG. 18A.

FIG. 18A illustrates a perspective view of an earbud 1800 with optical sensors according to some embodiments of the present disclosure. FIG. 18B illustrates a cross-sectional view of the earbud 1800 in FIG. 18A. The earbud 1800 includes two domes with dome flanges 1816. The emitter can be placed at location 1801 underneath a dome flange 1816. One or both of the dome flanges 1816 can be transparent for the wavelength used by the sensor.

Embodiments of the present disclosure are described with respect to positioning an emitter within a receiver-in-ear assembly. Similar concerns with positioning the emitter within the receiver-in-ear assembly exist for positioning a detector within the receiver-in-ear assembly. As such, various techniques and embodiments described can be combined for designing or achieving desired field of views for emitters and/or detectors.

All embodiments described in this patent applications are also working where there is direct (physical) contact between an optical transducer and human tissue.

The invention claimed is:
1. A hearing device comprising:
a housing comprising one or more wall portions defining an inner space and including a cavity extending through a wall portion of the housing;
a receiver provided in the inner space;
a circuit board layer;
an optical transducer mounted in the cavity, the optical transducer being mounted on the circuit board layer such that a spacing exists between a side of the optical transducer and a sidewall of the cavity; the circuit board layer extending underneath the wall portion and touching the wall portion such that the optical transducer is held within the cavity; and a protective substance forming a shield over the optical transducer and the cavity, the protective substance configured to affect a field of view of the optical transducer, the protective substance including one or more sealing glues sealing an inside of the cavity.

2. The hearing device of claim 1, wherein the sidewall of the cavity includes one or more step portions, one or more straight portions, one or more slanted portions, or any combination thereof.

3. The hearing device of claim 1, wherein the sidewall is curved or parabolic shaped.

4. The hearing device of claim 1, further comprising one or more reflective surfaces configured to reflect at least 30% of red, green, and/or near-infrared wavelengths and/or a wavelength of 850 nm.

5. The hearing device of claim 4, wherein the one or more reflective surfaces extends on an inner surface of the wall portion.

6. The hearing device of claim 4, wherein the one or more reflective surfaces extend along a surface of the optical transducer opposite to a surface of the optical transducer configured to transmit light.

7. The hearing device of claim 4, wherein the one or more reflective surfaces is on an outer surface of the wall portion or on the sidewall.

8. The hearing device of claim 4, wherein the one or more reflective surfaces include a material of reflective color, a plastic with reflective particles, metal, or any combination thereof.

9. The hearing device of claim 1, wherein the one or more sealing glues fill the cavity.

10. The hearing device of claim 9, wherein the protective substance fills the cavity and touches all sides of an optical transducer coating included in the optical transducer.

11. The hearing device of claim 1, wherein the protective substance includes a lens or a transparent material.

12. The hearing device of claim 1, wherein the protective substance includes a Fresnel lens, the Fresnel lens forming the shield as a flat surface.

13. The hearing device of claim 1, wherein the optical transducer comprises a radiating element positioned a predetermined distance from the circuit board layer.

14. The hearing device of claim 1, wherein the optical transducer comprises: a radiating element, a ceramic base, and glue.

15. The hearing device of claim 1, wherein the field of view of the optical transducer is further affected by a shape of the sidewall, a thickness of the housing, a curvature of the protective substance, a reflective layer, or any combination thereof.

16. The hearing device of claim 9, wherein the one or more sealing glues form the shield as an outwardly curved shield.

17. A method of manufacturing a hearing device that includes
a housing comprising one or more wall portions defining an inner space and including a cavity extending through a wall portion of the housing;
a receiver provided in the inner space;
a circuit board layer;
an optical transducer mounted in the cavity, the optical transducer being mounted on the circuit board layer such that a spacing exists between a side of the optical transducer and a sidewall of the cavity; the circuit board layer extending underneath the wall portion and touching the wall portion such that the optical transducer is held within the cavity; and
a protective substance forming a shield over the optical transducer and the cavity, the protective substance configured to affect a field of view of the optical transducer, the protective substance including one or more sealing glues sealing an inside of the cavity;
the method comprises:
applying the one or more sealing glues to fill spaces in the cavity in the housing.

18. The method of claim 17, wherein the applying step comprises applying the one or more sealing glues to contour the spaces within the cavity in the housing.

19. The method of claim 17, wherein the sidewall of the cavity includes one or more step portions enabling the one or more sealing glues to remain in the cavity during manufacturing.

20. A hearing device comprising:
a housing comprising one or more wall portions defining an inner space and including a cavity extending through a wall portion of the housing;
a receiver provided in the inner space;
a circuit board layer;
an optical transducer mounted in the cavity, the optical transducer being mounted on the circuit board layer such that a spacing exists between a side of the optical transducer and a sidewall of the cavity; the circuit board layer extending underneath the wall portion and touching the wall portion such that the optical transducer is held within the cavity, the optical transducer including a radiating element positioned a predetermined distance from the circuit board layer; and
a protective substance forming a shield over the optical transducer and the cavity, the protective substance configured to affect a field of view of the optical transducer.

21. A hearing device comprising:
a housing comprising one or more wall portions defining an inner space and including a cavity extending through a wall portion of the housing;
a receiver provided in the inner space;
a circuit board layer;
an optical transducer mounted in the cavity, the optical transducer being mounted on the circuit board layer such that a spacing exists between a side of the optical transducer and a sidewall of the cavity; the circuit board layer extending underneath the wall portion and touching the wall portion such that the optical transducer is held within the cavity, the optical transducer including a radiating element, a ceramic base, and a glue; and
a protective substance forming a shield over the optical transducer and the cavity, the protective substance configured to affect a field of view of the optical transducer.

* * * * *